US011521320B2

(12) United States Patent
Ohashi et al.

(10) Patent No.: US 11,521,320 B2
(45) Date of Patent: Dec. 6, 2022

(54) CONTROL DEVICE, CONTROL METHOD, AND PROGRAM

(71) Applicant: Sony Corporation, Tokyo (JP)

(72) Inventors: Takeshi Ohashi, Kanagawa (JP); Masataka Shinoda, Kanagawa (JP)

(73) Assignee: Sony Corporation, Tokyo (JP)

( * ) Notice: Subject to any disclaimer, the term of this patent is extended or adjusted under 35 U.S.C. 154(b) by 101 days.

(21) Appl. No.: 17/056,730

(22) PCT Filed: Apr. 5, 2019

(86) PCT No.: PCT/JP2019/015202
§ 371 (c)(1),
(2) Date: Nov. 18, 2020

(87) PCT Pub. No.: WO2019/225176
PCT Pub. Date: Nov. 28, 2019

(65) Prior Publication Data
US 2021/0201491 A1 Jul. 1, 2021

(30) Foreign Application Priority Data
May 25, 2018 (JP) .............................. JP2018-100358

(51) Int. Cl.
G06T 7/00 (2017.01)
G06N 20/00 (2019.01)
(Continued)

(52) U.S. Cl.
CPC ........... *G06T 7/0016* (2013.01); *C12M 41/46* (2013.01); *C12M 41/48* (2013.01); *G06F 3/14* (2013.01);
(Continued)

(58) Field of Classification Search
CPC ........ C12M 41/46; C12M 41/48; C12M 1/34; G06F 3/14; G06K 9/6256; G06N 20/00;
(Continued)

(56) References Cited

U.S. PATENT DOCUMENTS 9,053,222 B2* 6/2015 Lynn ...................... G16H 50/20
2014/0247972 A1 9/2014 Wang et al.
(Continued)

FOREIGN PATENT DOCUMENTS

CN 106661550 A * 5/2017 ............. A01K 67/02
CN 107771212 A * 3/2018 ............. C12M 23/10
(Continued)

OTHER PUBLICATIONS

International Search Report and English translation thereof dated Jul. 9, 2019 in connection with International Application No. PCT/JP2019/015202.

*Primary Examiner* — Ming Wu
(74) *Attorney, Agent, or Firm* — Wolf, Greenfield & Sacks, P.C.

(57) ABSTRACT

The technology is provided to effectively visualize culture statuses related to a plurality of culture targets.
Provided is a control device including a display control unit that controls dynamic display related to a culture status of a culture target including a cell having a division potential, the culture status being estimated along a time series by morphological analysis using a learned model generated on the basis of a machine learning algorithm, in which the display control unit controls comparative display of the culture statuses of a plurality of the culture targets. Furthermore, provided is a control method including controlling, by a processor, dynamic display related to a culture status of a culture target including a cell having a division potential, the culture status being estimated along a time series by morphological analysis using a learned model generated on the
(Continued)

basis of a machine learning algorithm, and controlling the display further including controlling comparative display of the culture statuses of a plurality of the culture targets.

20 Claims, 19 Drawing Sheets

(51) Int. Cl.

| | |
|---|---|
| *C12M 1/34* | (2006.01) |
| *C12M 1/36* | (2006.01) |
| *G06F 3/14* | (2006.01) |
| *G06K 9/62* | (2022.01) |
| *G06N 5/04* | (2006.01) |
| *G06T 11/20* | (2006.01) |

(52) U.S. Cl.
CPC ............. *G06K 9/6256* (2013.01); *G06N 5/04* (2013.01); *G06N 20/00* (2019.01); *G06T 11/206* (2013.01); *G06T 2207/20036* (2013.01); *G06T 2207/20076* (2013.01); *G06T 2207/20081* (2013.01); *G06T 2207/30024* (2013.01); *G06T 2207/30072* (2013.01)

(58) Field of Classification Search
CPC .......... G06N 5/04; G06N 3/0454; G06N 3/08; G06T 11/206; G06T 2207/20036; G06T 2207/20076; G06T 2207/20081; G06T 2207/30024; G06T 2207/30072; G06T 7/0016; G16H 50/20

See application file for complete search history.

(56) References Cited

U.S. PATENT DOCUMENTS

| | | | |
|---|---|---|---|
| 2014/0320513 A1 | 10/2014 | Ogi | |
| 2015/0306069 A1* | 10/2015 | Connell | ............... A61K 31/496 |
| | | | 514/254.02 |
| 2016/0370352 A1* | 12/2016 | Murrell | .................. A61K 35/32 |

FOREIGN PATENT DOCUMENTS

| | | |
|---|---|---|
| JP | 2016-509845 A | 4/2016 |
| JP | 2018-022216 A | 2/2018 |
| WO | WO 2013/099045 A1 | 7/2013 |
| WO | WO 2014/134550 A1 | 9/2014 |
| WO | WO 2018/025766 A1 | 2/2018 |

* cited by examiner

FIG. 1
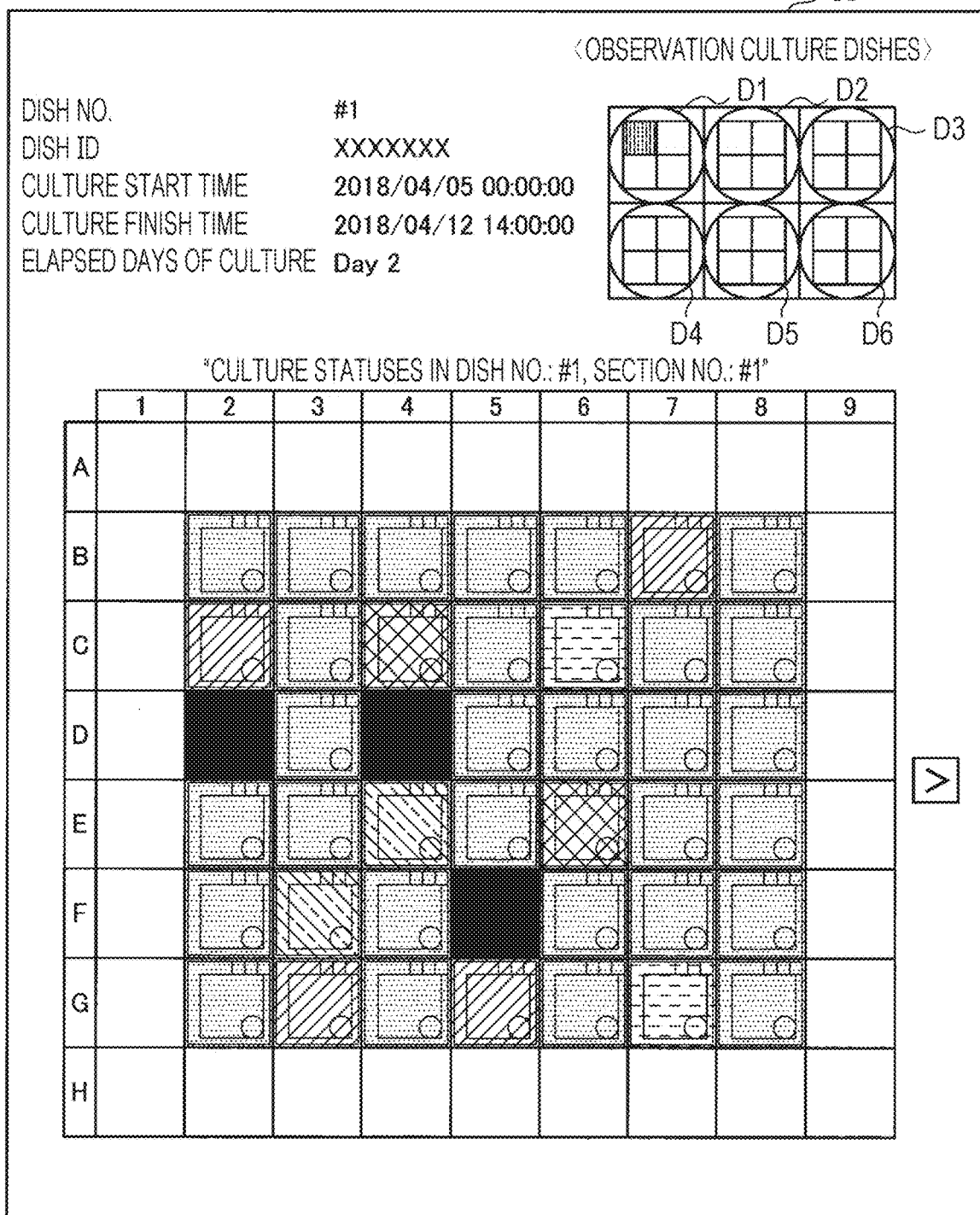
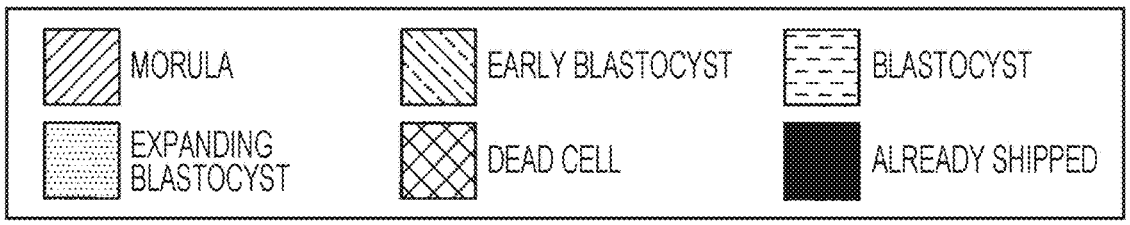

*FIG. 5*

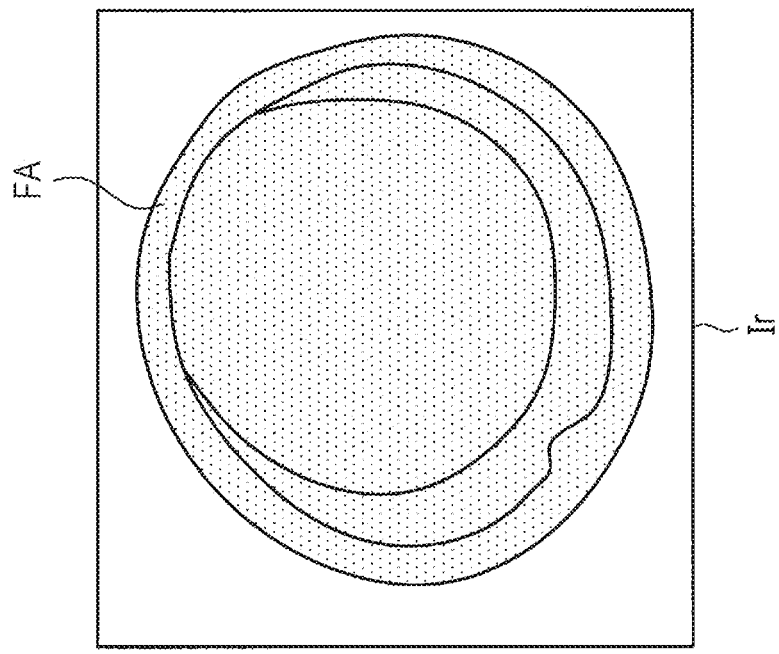
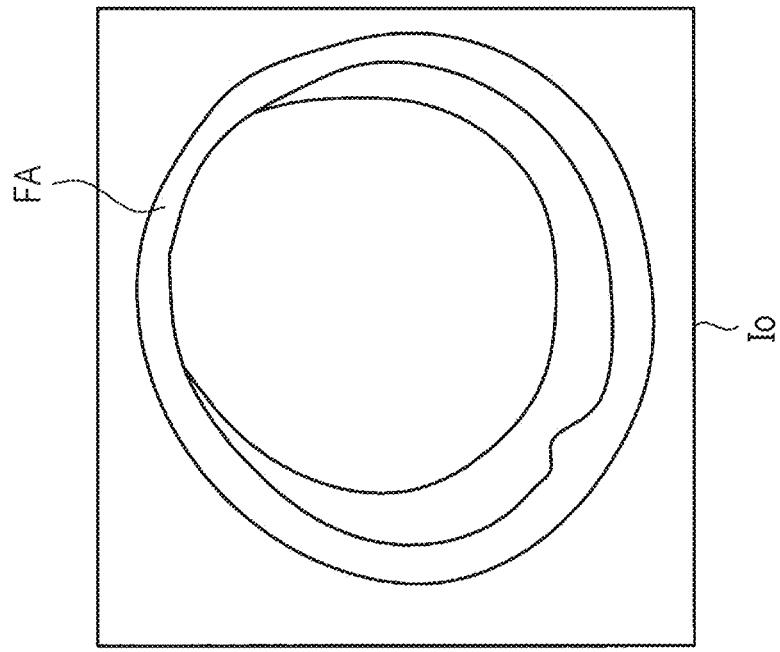
FIG. 18

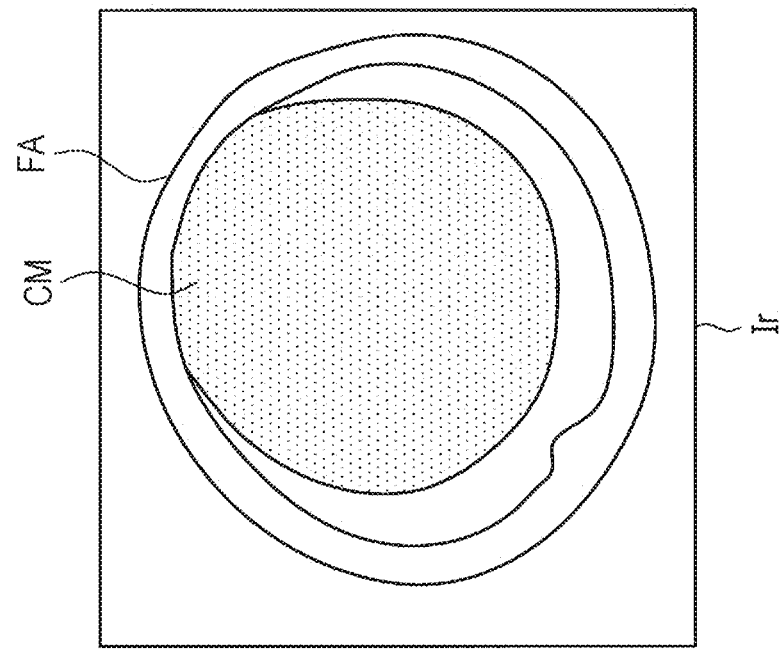
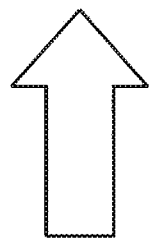
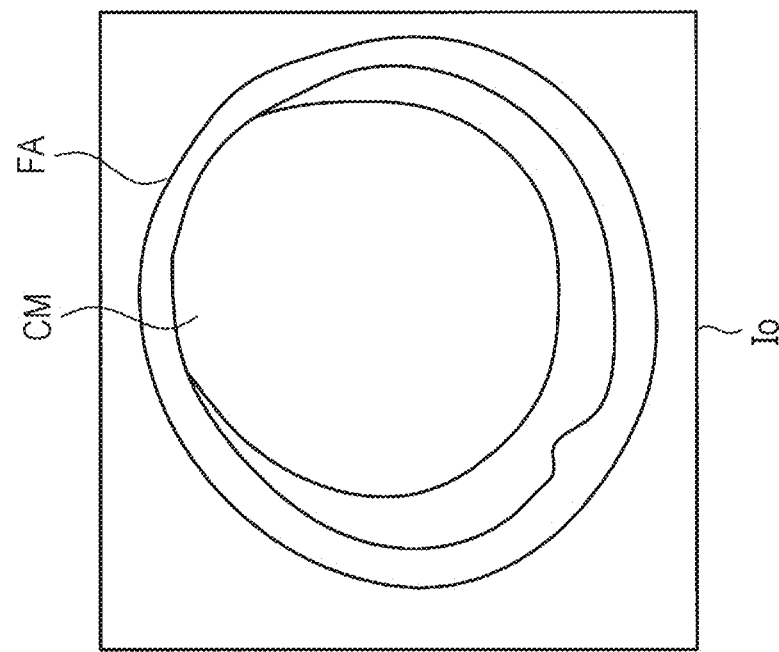
FIG. 20

CONTROL DEVICE, CONTROL METHOD, AND PROGRAM

CROSS-REFERENCE TO RELATED APPLICATIONS

This application claims the benefit under 35 U.S.C. § 371 as a U.S. National Stage Entry of International Application No. PCT/JP2019/015202, filed in the Japanese Patent Office as a Receiving Office on Apr. 5, 2019, which claims priority to Japanese Patent Application Number JP2018-100358, filed in the Japanese Patent Office on May 25, 2018, each of which is hereby incorporated by reference in its entirety.

TECHNICAL FIELD

The present disclosure relates to a control device, a control method, and a program.

BACKGROUND ART

In recent years, a technique of capturing images of a cell or the like along a time series and observing temporal changes in the cell has been widely used. For example, Patent Document 1 discloses a technology of estimating a stage related to division of a cell to be a culture target.

CITATION LIST

Patent Document

Patent Document 1: Japanese Translation of PCT International Application Publication No. 2016-509845

SUMMARY OF THE INVENTION

Problems to be Solved by the Invention

By the way, in observation of a culture target, such as a cell, it is general to culture a large number of cells at the same time and perform observation and evaluation thereon. However, sufficient consideration has not given to presentation of observation results and evaluation results of a plurality of culture targets in the technology disclosed in Patent Document 1.

Accordingly, the present disclosure proposes a control device, a control method, and a program which are novel, improved, and capable of effectively visualizing culture statuses related to a plurality of culture targets.

Solutions to Problems

According to the present disclosure, provided is a control device including a display control unit that controls dynamic display related to a culture status of a culture target including a cell having a division potential, the culture status being estimated along a time series by morphological analysis using a learned model generated on the basis of a machine learning algorithm, in which the display control unit controls comparative display of the culture statuses of a plurality of the culture targets.

Furthermore, according to the present disclosure, provided is a control method including controlling, by a processor, dynamic display related to a culture status of a culture target including a cell having a division potential, the culture status being estimated along a time series by morphological analysis using a learned model generated on the basis of a machine learning algorithm, and controlling the display further including controlling comparative display of culture statuses of a plurality of the culture targets.

Moreover, according to the present disclosure, provided is a program causing a computer to function as a control device including a display control unit that controls dynamic display related to a culture status of a culture target including a cell having a division potential, the culture status being estimated along a time series by morphological analysis using a learned model generated on the basis of a machine learning algorithm, in which the display control unit controls comparative display of the culture statuses of a plurality of the culture targets.

Effects of the Invention

As described above, according to the present disclosure, it is possible to effectively visualize culture statuses related to the plurality of culture targets.

Note that the above-described effect is not necessarily limited, and any effect described in the present specification or another effect that can be grasped from the present specification may also be exerted in addition to the above-described effect or instead of the above-described effect.

BRIEF DESCRIPTION OF DRAWINGS

FIG. 1 is an exemplary user interface controlled by a display control unit according to an embodiment of the present disclosure.

FIG. 5 is a diagram illustrating exemplary display of cleavage timing of a fertile ovum and an elapsed time after the cleavage according to the same embodiment.

FIG. 18 is a diagram to describe generation of an overlay image according to the same embodiment.

FIG. 20 is a diagram to describe generation of an overlay image of a constituent included in a culture target according to the present embodiment according to the same embodiment.

MODE FOR CARRYING OUT THE INVENTION

Figure 2:
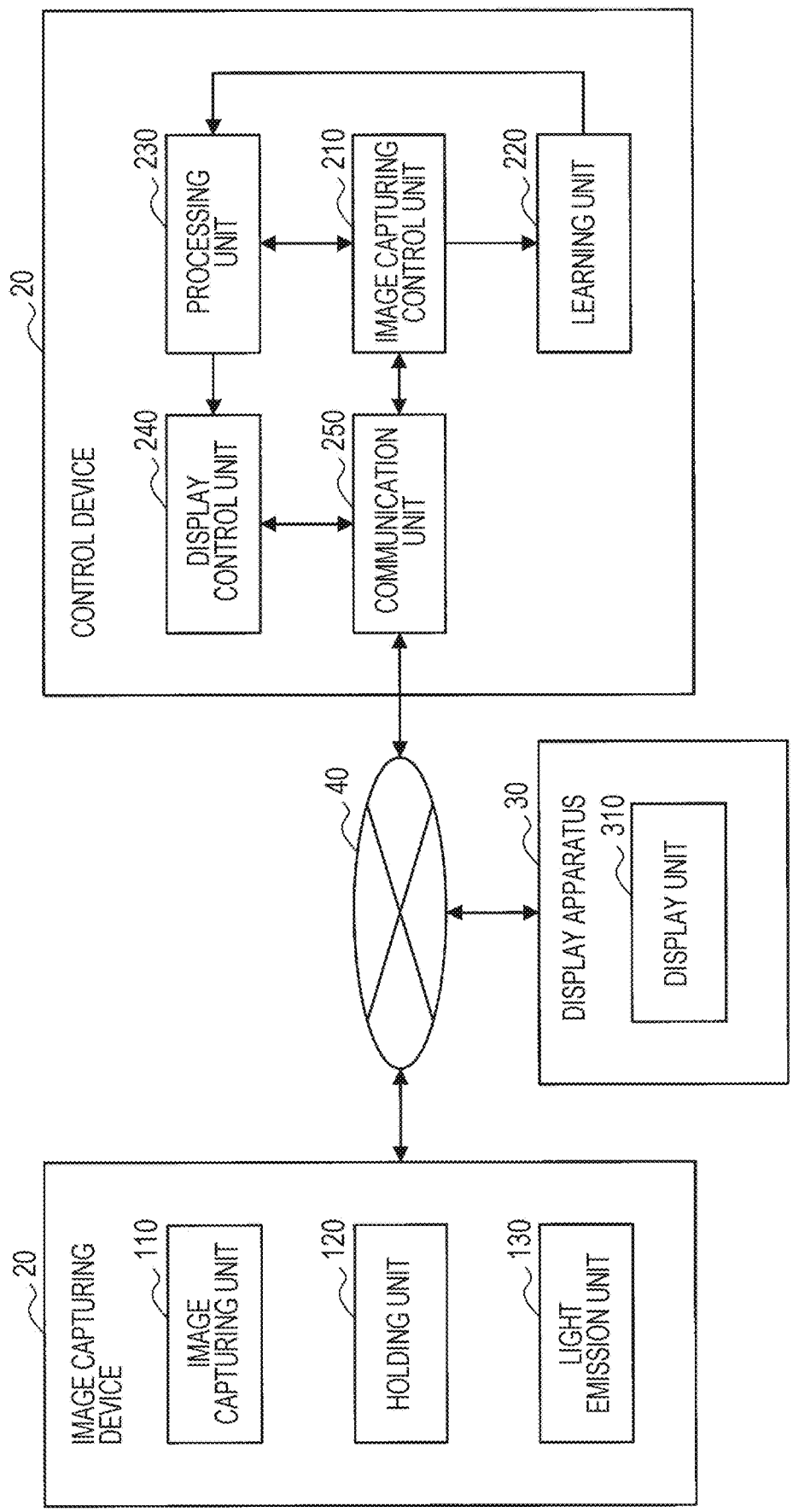
FIG. 2 is a block diagram illustrating an exemplary functional configuration of a control system according to the same embodiment.

In the following, a preferred embodiment of the present disclosure will be described in detail with reference to the accompanying drawings. Note that, in the present specification and the drawings, constituent elements having substantially the same functional configuration will be denoted by the same reference sign, and duplicate description will be omitted.

Note that the description will be provided in the following order.
1. Embodiment
1.1. Outline
1.2. Exemplary Configuration
1.3. Details of Functions
1.4. Operation Flow
2. Exemplary Hardware Configuration
3. Conclusion 1. Embodiment 1.1. Outline First, an outline of an embodiment of the present disclosure will be described. As described above, in recent years, a technique of capturing images of a culture target such as a cell along a time series (also referred to as time-lapse image capturing) and observing temporal changes in the cell is widely used in various field.

For example, the field of livestock performs a technique of observing temporal changes in a fertile ovum of livestock or the like by performing the time-lapse image capturing when the fertile ovum is grown to a transplantable state, and evaluating a growth state.

Furthermore, there has been also a developed technology in which a system semi-automatically performs the time-lapse image capturing and the evaluation on the growth state as described above. However, even in a case where the image capturing and the evaluation are performed by the system, it is general that an embryologist finally confirms the evaluation determined by the system, and shipment determination is made, for example, after the evaluation result is corrected as necessary.

However, there is a case where a large number of fertile ova such as 1000 to 2000 fertile ova are observed and evaluated at the same time in the time-lapse image capturing as described above, and a heavy workload and a long time are required for an embryologist to perform re-evaluation and shipment determination related to all of the fertile ova. Furthermore, the time-lapse image capturing is performed for a long time not only in the field of livestock but also in fields of infertility treatment, regenerative medical treatment, and the like, but it has been extremely difficult to intuitively grasp culture statuses related to a large number of culture targets.

A technical idea according to the present disclosure is conceived focusing on the above-described points, and is directed to achieving effective visualization of culture statuses related to a plurality of culture targets. For this, a control device 20 that implements a control method according to an embodiment of the present disclosure includes a display control unit 240 that controls dynamic display related to a culture status of a culture target including a cell having a division potential, in which the culture status is estimated along a time series by morphological analysis using a learned model generated on the basis of a machine learning algorithm. Furthermore, the display control unit 240 according to the embodiment of the present disclosure has a characteristic of controlling comparative display of the culture statuses of a plurality of culture targets.

FIG. 1 is an exemplary user interface UI controlled by the display control unit 240 according to the embodiment of the present disclosure. Note that FIG. 1 illustrates the exemplary user interface UI in a case where a culture target according to the present embodiment is a fertile ovum.

As illustrated in FIG. 1, for example, time-lapse images of a plurality of fertile ova captured by an image capturing device 10 are displayed in an array on the user interface UI controlled by the display control unit 240 according to the present embodiment. Furthermore, the time-lapse image of each fertile ovum may be added with a culture status estimated by a processing unit 230 according to the present embodiment by the morphological analysis using the learned model generated on the basis of the machine learning algorithm.

For example, in the case where the culture target is a fertile ovum, the above-described culture status includes a cleavage status of the fertile ovum. Additionally, the above-described cleavage status may include, for example, a cleavage stage of the fertile ovum and an occurrence status of abnormal cleavage. Furthermore, the above-described culture status may include, for example, a status related to a dead cell of the fertile ovum. Moreover, a status related to a fertile ovum that has been already shipped may also be included.

In the exemplary case illustrated in FIG. 1, the display control unit 240 according to the present embodiment comparatively displays, by using an overlay color of each time-lapse image, a status related to a cleavage stage, a dead cell, or completion of shipment of a fertile ovum estimated by the processing unit 230. Note that the above-described cleavage stage includes, for example, a morula, an early blastocyst, a blastocyst, an expanding blastocyst, or the like.

Thus, with the display control unit 240 according to the present embodiment, culture statuses related to a large amount of fertile ova can be presented to a user such as an embryologist in a comparative state.

Furthermore, at this time, the display control unit 240 according to the present embodiment may perform control such that time-lapse images and culture statuses related to the plurality of fertile ova are displayed in a manner correlated to well positions (coordinates) where the fertile ova are arranged in a culture dish.

For example, referring to the upper right of the diagram of FIG. 1, it can be seen that a time-lapse image currently displayed on the user interface UI is correlated to a fertile ovum cultured in an upper left section of a culture dish D1 on the upper left out of six culture dishes D1 to D6. Furthermore, the display control unit 240 may perform control such that each time-lapse image is displayed in a manner correlated to a physical position of each fertile ovum in the above-described region.

Thus, the display control unit 240 according to the present embodiment can display culture statuses of a large amount of culture targets in a manner correlated to the well positions where the culture targets are arranged in the culture dish. The above-described function of the display control unit 240 according to the present embodiment enables a user such as an embryologist to: intuitively grasp a culture status related to each of the fertile ova; and accurately determine shipment and the like in a short time.

In the above, the description has been provided for the outline of the comparative display of culture statuses related to culture targets under the control of the display control unit 240 according to the present embodiment. Note that the case where the culture target is a fertile ovum has been described as an example in the above description using FIG. 1, but the culture target according to the present embodiment may widely include cells each having a division potential. Note that examples of the cell having the division potential can include: a cancer cell; various culture cells used in the field of regenerative medicine and the like; and so on.

Furthermore, in the present specification, a "fertile ovum" at least conceptually includes:

a single cell; and an aggregate of a plurality of cells. Here, the single cell or the aggregate of a plurality of cells is associated with a cell observed in one or a plurality of stages including an oocyte, an egg or an ovum, a fertile ovum or a zygote, an undifferentiated embryo cell (blastocyst), and an embryo in a growth process of a fertile ovum.

1.2. Exemplary Configuration

Next, an exemplary configuration of a control system according to the present embodiment will be described. FIG. 2 is a block diagram illustrating an exemplary functional configuration of the control system according to the present embodiment. Referring to FIG. 2, the control system according to the present embodiment includes the image capturing device 10, the control device 20, and a display apparatus 30. Furthermore, the image capturing device 10 and the control device 20, and the control device 20 and the display apparatus 30 are each connected respectively via a network 40 so as to be able to communicate with each other.

(Image Capturing Device 10)

The image capturing device 10 according to the present embodiment is a device that captures an image of a culture target such as a fertile ovum on the basis of control by the control device 20. The image capturing device 10 according to the present embodiment may be, for example, an optical microscope having an image capturing function, or the like.

Referring to FIG. 2, the image capturing device 10 according to the present embodiment includes an image capturing unit 110, a holding unit 120, and a light emission unit 130.

((Image Capturing Unit 110))

The image capturing unit 110 according to the present embodiment has a function of capturing an image of a culture target on the basis of the control by the control device 20. The image capturing unit 110 according to the present embodiment is implemented by, for example, an image capturing device such as a camera. Furthermore, the image capturing unit 110 may include a plurality of optical objective lenses having different magnifications.

The control device 20 according to the present embodiment can control: image capturing timing, an image capturing time (an exposure time), and selection of an optical objective lens of the image capturing unit 110; a physical position in a horizontal direction or a vertical direction of the image capturing unit 110; and the like.

((Holding Unit 120))

The holding unit 120 according to the present embodiment has a function of holding a culture dish where a culture target is cultured. The holding unit 120 according to the present embodiment can be, for example, an observation stage.

The control device 20 according to the present embodiment can control a horizontal position or a focus position of a culture target during the image capturing by controlling the physical position or the like in the horizontal position or the vertical direction of the holding unit 120.

((Light Emission Unit 130))

The light emission unit 130 according to the present embodiment has a function of emitting various kinds of light to be used in the image capturing on the basis of the control by the control device 20. Furthermore, the light emission unit 130 according to the present embodiment may widely include an optical system such as an aperture stop.

The control device 20 according to the present embodiment can control a kind, a wavelength, intensity, a light emission time, a light emission interval, and the like of the light emitted by the light emission unit 130.

(Control Device 20) The control device 20 according to the present embodiment has a function of controlling image capturing of a culture target on the basis of a recognition probability of the culture target, the recognition probability being calculated by using the learned model generated on the basis of the machine learning algorithm. The control device 20 according to the present embodiment is mounted as, for example, an information processing server and may remotely control the image capturing device 10 via the network 40.

Furthermore, the control device 20 according to the present embodiment has functions of: dynamically estimating, along a time series, a culture status of a culture target by the morphological analysis using the learned model generated on the basis of the machine learning algorithm; and controlling comparative display of the culture statuses.

((Image Capturing Control Unit 210))

The image capturing control unit 210 according to the present embodiment has a function of controlling time-lapse image capturing of a culture target by the image capturing device 10. The image capturing control unit 210 according to the present embodiment has a characteristic of controlling, for example, a relative horizontal position and a focal position between the image capturing unit 110 and an observation target on the basis of a recognition probability of the observation target calculated by using the learned model generated on the basis of the machine learning algorithm.

((Learning Unit 220))

The learning unit 220 according to the present embodiment has a function of performing learning related to, for example, recognition of an observation target on the basis of: an image obtained by capturing an image of a culture target; and the machine learning algorithm. The learning unit 220 according to the present embodiment may perform recognition learning of the observation target by, for example, machine learning using a multi-layer neural network such as Deep Learning that includes a plurality of convolution layers.

The learning unit 220 according to the present embodiment can learn characteristics related to a shape, a morphology, a structure, and the like of a culture target by performing, for example, supervised learning based on: an image obtained by image capturing of the culture target; and training data. Note that the above-described training data may include, for example, information related to: a classification of a culture target included in an image (e.g., a fertile ovum or the like); and a growth stage of the culture target (e.g., a cleavage stage such as two cells, four cells, a morula, an early blastocyst, a blastocyst, or an expanding blastocyst, or a dead cell). That is, the learning unit 220 may perform machine learning (for example, the machine learning by the multi-layer neural network) and may generate a learned model that recognizes a culture target by using learning data including: an image obtained by image capturing of a culture target; and the above-described training data (information associated with the characteristic related to at least one of a shape, a morphology, a structure, or the like of the culture target). That is, for example, in the case of the machine learning by the multi-layer neural network, a weighting factor (parameter) between respective layers including an input layer, an output layer, and a hidden layer constituting the neural network is adjusted by the above-described learning, and consequently, the learned model is generated.

((Processing Unit 230))

The processing unit 230 according to the present embodiment has a function of performing the morphological analysis on a culture target on the basis of learned knowledge learned by the learning unit 220. That is, the processing unit 230 according to the present embodiment may be a recognizer (also referred to as a classifier) generated from the learning by the learning unit 220. The processing unit 230 according to the present embodiment, for example, receives an image of a culture target as an input and can output, in a time series, a probability value related to a cleavage stage of a fertile ovum by the morphological analysis using the learned model generated on the basis of the machine learning algorithm. The details of the functions included in the processing unit 230 according to the present embodiment will be separately described later.

((Display Control Unit 240))

The display control unit 240 according to the present embodiment has a function of controlling dynamic display related to a culture status of a culture target estimated by the processing unit 230 along a time series by the morphological analysis. The display control unit 240 according to the present embodiment may control comparative display of particularly culture statuses related to a plurality of culture targets.

As described above, the above-described culture target includes, for example, a fertile ovum. At this time, the display control unit 240 according to the present embodiment can control the display apparatus 30 such that cleavage statuses or a dead cell/dead cells of the plurality of fertile ova are comparatively displayed.

Furthermore, the above-described cleavage status includes a cleavage stage of a fertile ovum, and an occurrence status of abnormal cleavage or a lag-phase, as described above. The display control unit 240 according to the present embodiment can control the display apparatus 30 such that the cleavage stages of the plurality of fertile ova and the occurrence status of the abnormal cleavage are displayed comparatively.

Note that the display control unit 240 according to the present embodiment may control, on the user interface as illustrated in FIG. 1, the comparative display of the culture statuses as described above. The user interface according to the present embodiment may be implemented in a form of a Web service or the like, for example. A user can confirm, for example, a culture status of each culture target via the user interface displayed by the display apparatus 30, and can further perform various actions such as recording a determination result. At this time, the display control unit 240 generates, for example, control information such as an HTML file that defines a display format of the user interface, and transmits the control information to the display apparatus 30 via the communication unit 250, thereby achieving control of the display on the user interface by the display apparatus 30. The details of the functions of the display control unit 240 according to the present embodiment will be separately described later.

(Communication Unit 250) The communication unit 250 according to the present embodiment has a function of performing information communication with the image capturing device 10 and the display apparatus 30 via the network 40. The communication unit 250 according to the present embodiment transmits, to the image capturing device 10, a control signal that is generated by, for example, the image capturing control unit 210 and related to image capturing control, and receives a captured image of a culture target from the image capturing device 10. Furthermore, the communication unit 250 according to the present embodiment transmits, to the display apparatus 30, control information that is generated by the display control unit 240 and related to display control of the user interface.

(Display Apparatus 30) The display apparatus 30 according to the present embodiment is a device that performs comparative display of culture statuses related to the plurality of culture targets on the basis of the control by the control device 20.

((Display Unit 310))

The display unit 310 according to the present embodiment has a function of outputting visual information such as an image and text. The display unit 310 according to the present embodiment particularly displays the user interface that allows a user to confirm a culture status of a culture target on the basis of the control information received from the control device 20. On the other hand, the display unit 310 according to the present embodiment may have a function equivalent to that of the display control unit 240 of the control device 20. In this case, the display unit 310 receives various recognition results output from the processing unit 230 of the control device 20, and can control the display of the user interface on the basis of the recognition results.

For this, the display unit 310 according to the present embodiment includes, for example, a display device that presents the visual information. Examples of the above-described display device may include a liquid crystal display (LCD) device, an organic light emitting diode (OLED) device, a touch panel, and the like.

(Network 40) The network 40 has a function of connecting the image capturing device 10 and the control device 20. The network 40 may include: public line networks such as the Internet, a telephone line network, and a satellite communication network; and various kinds of networks including the Ethernet (registered trademark), such as a local area network (LAN), and a wide area network (WAN). Furthermore, the network 40 may include a dedicated line network such as an internet protocol-virtual private network (IP-VPN). Furthermore, the network 40 may include a wireless communication network such as Wi-Fi (registered trademark) and Bluetooth (registered trademark).

In the above, the exemplary configuration of the control system according to the present embodiment has been described. Note that the configurations of the image capturing device 10 and the control device 20 according to the present embodiment are not limited to the exemplary configurations described above by using FIG. 2. For example, the control device 20 according to the present embodiment does not necessarily include the learning unit 220. The control device 20 according to the present embodiment may control the image capturing by the image capturing device 10 or may estimate a culture state related to a culture target on the basis of learned knowledge learned by another device. The functional configurations of the control system and the control device 20 according to the present embodiment can be flexibly modified in accordance with specifications and actual use.

1.3. Details of Functions

Next, the functions of the control device 20 according to the present embodiment will be described in detail. First, comparative display control of culture statuses by the display control unit 240 according to the present embodiment will be described.

As described above, the display control unit 240 according to the present embodiment controls the comparative display of the culture statuses related to the plurality of culture targets. In FIG. 1, the case where the display control unit 240 according to the present embodiment controls the comparative display of the statuses related to the cleavage stages and the dead cell(s) of the fertile ova as the examples of the culture statuses. On the other hand, the display control unit 240 according to the present embodiment is not limited to the above-described example and may control the comparative display related to various culture statuses.

Figure 3:
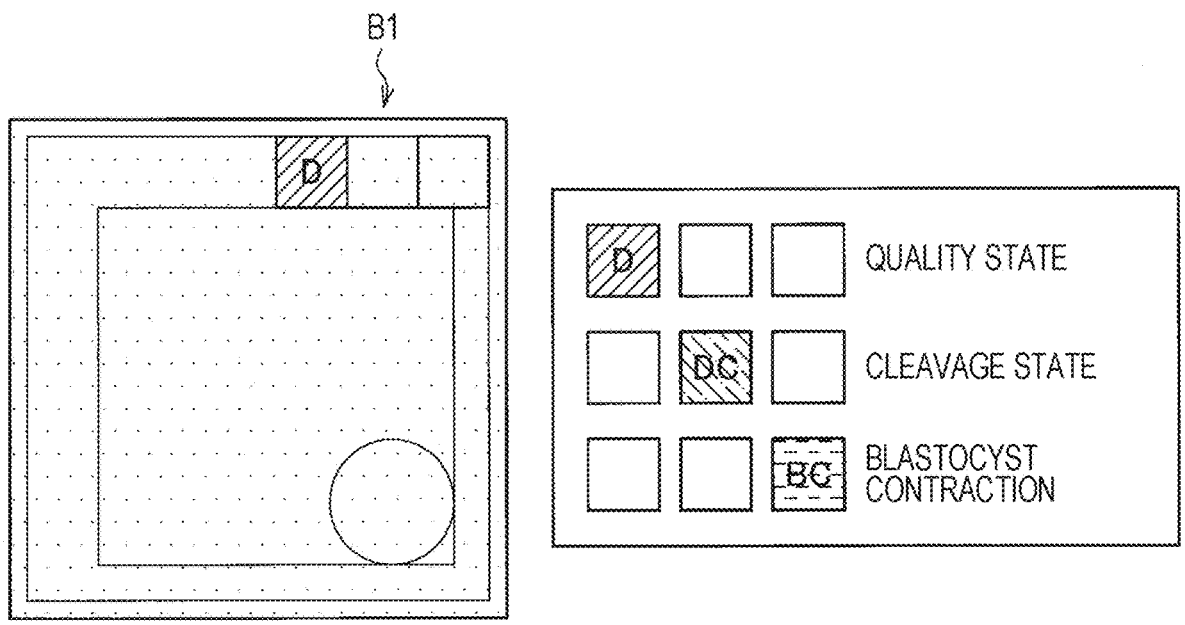
FIG. 3 is a diagram to describe comparative display control of a culture status related to a culture target by a display control unit according to the same embodiment.

FIG. 3 is a diagram to describe comparative display control of a culture status related to a culture target by the display control unit 240 according to the present embodiment. In an exemplary case illustrated in FIG. 3, the display control unit 240 according to the present embodiment implements the comparative display of culture statuses by adding a box B1 that indicates various kinds of the culture status at the upper right of a time-lapse image displayed on the user interface UI illustrated in FIG. 1.

Specifically, in the example illustrated in FIG. 3, the display control unit 240 adds, to a left frame of the box B1, a color or a character indicating a quality state of a fertile ovum. Here, the above-described quality state may comprehensively indicate a culture state of a fertile ovum. The display control unit 240 can indicate, for example, a fact that a fertile ovum corresponding to a time-lapse image is normally growing, a fact that the fertile ovum has become a dead cell, and the like by using different colors, characters, marks, and the like. In the exemplary case illustrated in FIG. 3, the display control unit 240 indicates, by using a predetermined color and a character "D", a fact that the fertile ovum corresponding to the time-lapse image has become a dead cell.

Furthermore, in the example illustrated in FIG. 3, the display control unit 240 adds, to a center frame of the box B1, a color and a character indicating a cleavage status of the fertile ovum. The above-described cleavage status includes, for example, the cleavage stage and the occurrence status of abnormal cleavage. The display control unit 240 can display, for example, a fact that the fertile ovum corresponding to the time-lapse image is normally cleaved, a fact that abnormal cleavage has occurred, a kind of the cleavage stage, a kind of the abnormal cleavage, and the like by using an indicator such as a color, a character, and a mark.

In the exemplary case illustrated in FIG. 3, the display control unit 240 indicates, by using a predetermined color and characters "DC", a fact that direct cleavage has occurred in the fertile ovum corresponding to the time-lapse image.

Here, the above-described direct cleavage is a kind of the abnormal cleavage in which a fertile ovum is divided by a non-constant number, for example, division from one cell to three cells, from two cells to six cells, or the like. It is known that a fertility rate of a fertile ovum that has undergone the direct cleavage is significantly lower than that of a fertile ovum that has been normally divided by a constant number.

Furthermore, the abnormal cleavage according to the present embodiment includes not only the above-described direct cleavage but also reverse cleavage in which a cleavage stage of a fertile ovum retrogrades like, for example, from three cells to two cells, or eight cells to six cells. Similar to the fertility rate of the fertile ovum that has undergone the direct cleavage, it is known that a fertility rate of a fertile ovum that has undergone the reverse cleavage is significantly lower than that of the fertile ovum that has been normally divided by a constant number.

Thus, the display control unit 240 according to the present embodiment enables an embryologist to: intuitively and easily grasp, from among the plurality of fertile ova, a fertile ovum in which the abnormal cleavage such as the direct cleavage or the reverse cleavage has occurred; and take a measure such as removing this fertile ovum before shipment, and the like.

Furthermore, in the example illustrated in FIG. 3, the display control unit 240 adds, to a right frame of the box B1, a color or a character indicating another culture status related to a fertile ovum. In the exemplary case illustrated in FIG. 3, the display control unit 240 indicates, by using a predetermined color and characters "BC", a fact that blastocyst contraction has occurred in the fertile ovum corresponding to the time-lapse image.

As described above, the display control unit 240 according to the present embodiment can display various kinds of information related to a culture status of a fertile ovum by using the colors, the characters, the marks, and the like. The above-described function of the display control unit 240 according to the present embodiment enables a user such as an embryologist to exhaustively and integrally grasp the culture statuses related to the plurality of fertile ova, and it is possible to largely reduce a time, man-hours, the number of persons, and the like required for determination.

Next, display control related to a determination state of a fertile ovum according to the present embodiment will be described. As described above, even in the case of performing automatic determination for the large number of fertile ova by the time-lapse image capturing, it is general that an embryologist finally confirms a state of each fertile ovum and makes determination related to shipment and the like.

However, at this time, there is a case where it is difficult for the embryologist to instantly judge which one of the large number of displayed fertile ova has been already subjected to primary determination or final determination.

Accordingly, the display control unit 240 according to the present embodiment can assist, by adding a state related to determination on a fertile ovum, and the like to a time-lapse image, the embryologist to perform the above-described judgment.

Figure 4:
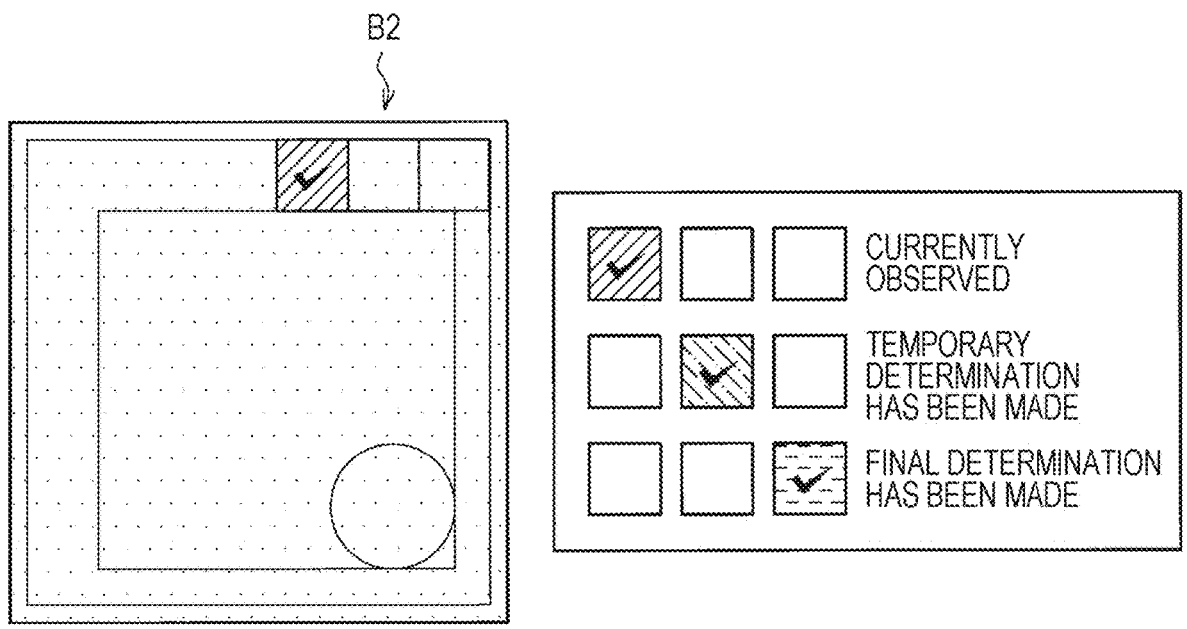
FIG. 4 is a diagram to describe the comparative display control for a state related to determination on a fertile ovum according to the same embodiment.

FIG. 4 is a diagram to describe the comparative display control for a state related to determination on a fertile ovum according to the present embodiment. In an exemplary case illustrated in FIG. 4, the display control unit 240 according to the present embodiment implements comparative display of a determination state by adding a box B2 indicating a state related to determination on a fertile ovum to the upper right of each time-lapse image displayed on the user interface UI illustrated in FIG. 1.

Specifically, in a case where determination related to the fertile ovum has not been made yet, the display control unit 240 adds a predetermined color and a mark to a left frame of the box B2. Furthermore, in a case where a temporary determination on the fertile ovum has been made, the display control unit 240 adds a predetermined color and a mark to a center frame of the box B2, and in a case where the final determination on the fertile ovum has been made, the display control unit 240 adds a predetermined color and a mark to a right frame of the box B2.

The above-described function of the display control unit 240 according to the present embodiment enables an embryologist to instantly grasp determination states of the fertile ova and efficiently perform determination work even in the case of observing the large number of fertile ova at the same time.

In the above, the comparative display control by the display control unit 240 according to the present embodiment has been described. As described above, the display control unit 240 according to the present embodiment can present, to a user, culture statuses, judgment states, and the like related to the plurality of fertile ova in a comparative state by using the indicators such as the colors, the characters, or the marks. Note that the comparative display control by the display control unit 240 according to the present embodiment is not limited to the examples described above, and can be implemented by various forms.

For example, in FIG. 1, the description has been provided by exemplifying the case where the display control unit 240 according to the present embodiment indicates a cleavage stage or the like by overlaying a color on a time-lapse image, but the display control unit 240 may also indicate a culture status of a fertile ovum by, for example, varying a frame color, a pattern, an emphasis degree of a time-lapse image. Furthermore, the display control unit 240 does not necessarily display a time-lapse image of a fertile ovum, and may indicate a culture status using an ID and the like corresponding to each fertile ovum, for example.

Next, detailed display control of a culture state related to a fertile ovum by the display control unit 240 according to the present embodiment will be described. In a case where a user selects a time-lapse image displayed on the user interface UI, for example, the display control unit 240 according to the present embodiment may control movement to a detail page that displays detailed data of a culture state of a fertile ovum corresponding the time-lapse image.

The display control unit 240 according to the present embodiment may control information display related to, for example, cleavage timing of a fertile ovum, an elapsed time after the cleavage, and the like on the above-described detail page. At this time, the display control unit 240 according to the present embodiment may control time-series display related to a culture status of a fertile ovum on the basis of an estimation result by the processing unit 230.

Figure 5:
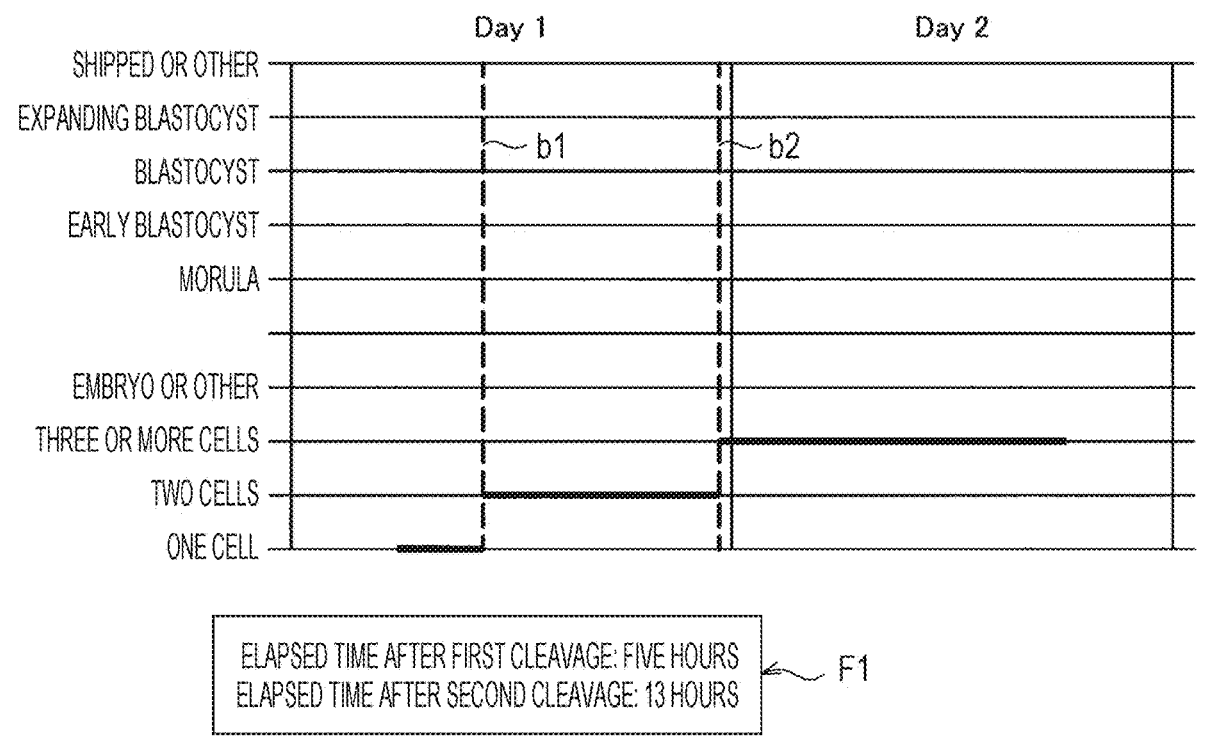

FIG. 5 is a diagram illustrating exemplary display of cleavage timing of a fertile ovum and an elapsed time after the cleavage according to the present embodiment. In the example illustrated in FIG. 5, the display control unit 240 displays, by a graph, transition between the cleavage stages of the fertile ovum in a time series on the basis of probability values calculated by the processing unit 230 and related to each cleavage stage of the fertile ovum.

For example, the exemplary case illustrated in FIG. 5 indicates a fact that the fertile ovum is cleaved from one cell to two cells and then from two cells to three or more cells on "Day 1". At this time, the display control unit 240 can indicate cleavage timing estimated by the processing unit 230 and related to the above by adding, for example, bars b1 and b2 onto the graph.

Furthermore, the above-described bars b1 and b2 can be corrected by, for example, slide action by a user. In a case where a user such as an embryologist confirms the graph and judges that the cleavage timing is erroneously estimated, the determination can be corrected by sliding a position of the bar b1 or b2.

Furthermore, the display control unit 240 calculates an elapsed time after first cleavage or an elapsed time after second cleavage on the basis of the positions of the bars b1 and b2 and may display the calculated elapsed time in a field F1.

Thus, the display control unit 240 according to the present embodiment enables the embryologist to easily confirm the cleavage timing and the elapsed time after the cleavage of the fertile ovum and correct the same.

Furthermore, the display control unit 240 according to the present embodiment may control, for example, information display related to a lag-phase of a fertile ovum. Generally, it is known that a fertile ovum has the lag-phase (also called an induction phase) during which active proliferation of a cell stops. Furthermore, in recent years, it is revealed that the lag-phase occurs in a division process from a four-cell phase to an eight-cell phase, and the larger the number of cells there is at start of the lag-phase, the earlier the start time is, and the shorter a period of the lag-phase of a fertile ovum is, the higher developmental potency (e.g., fertility rate) the fertile ovum has after transplantation.

Due to the above-described circumstances, the lag-phase of each fertile ovum is focused as an important index to identify a fertile ovum having the high developmental potency.

Therefore, the display control unit 240 according to the present embodiment can assist, by displaying the information related to the lag-phase estimated by the processing unit 230, an embryologist to perform comprehensive quality determination on a fertile ovum.

Figure 6:
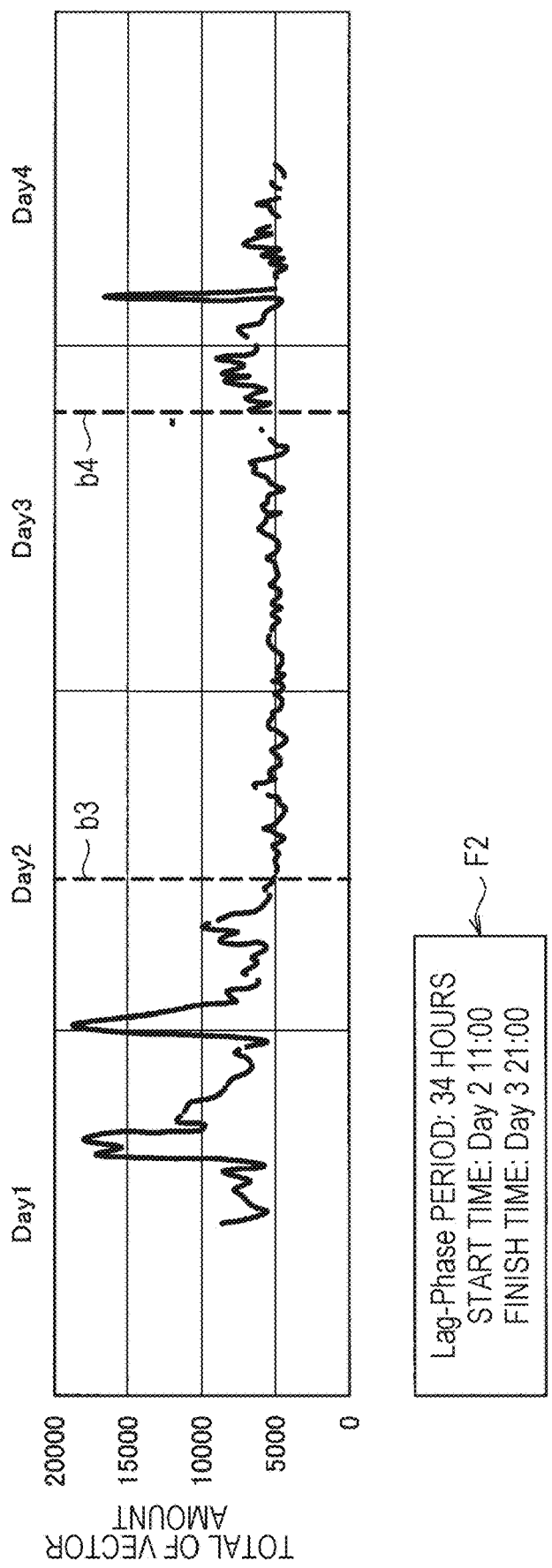
FIG. 6 is a diagram illustrating exemplary display of information related to a lag-phase of a fertile ovum according to the same embodiment.

FIG. 6 is a diagram illustrating exemplary display of the information related to a lag-phase of a fertile ovum according to the present embodiment. In the example illustrated in FIG. 5, the display control unit 240 displays, on a graph, bars b3 and b4 representing start and finish of the lag-phase estimated by the processing unit 230 on the basis of a change in a movement amount of a cell (a total value of velocity vectors) inside the fertile ovum calculated by the processing unit 230, the graph visualizing the change in the above-described movement amount.

For example, the processing unit 230 according to the present embodiment can estimate, as the lag-phase, an overlap period between a period during which a temporal change in the total value of the above-described movement amount per unit culture time is a threshold or less and a period during which a temporal change in a diameter of the fertile ovum per unit culture time is a threshold or less.

Furthermore, at this time, the display control unit 240 according to the present embodiment receives slide action to the bars b3 and b4 in a manner similar to the case illustrated in FIG. 5, and may perform control such that an embryologist who has confirmed the graph can correct the lag-phase.

Furthermore, the display control unit 240 may display, in a field F2, a total period, the start time, the finish time, and the like of the lag-phase on the basis of positions of the bars b3 and b4.

Thus, the display control unit 240 according to the present embodiment enables the embryologist to easily confirm and correct the lag-phase of each fertile ovum.

Furthermore, for example, the display control unit 240 according to the present embodiment may display, on the same graph, a cleavage stage of a fertile ovum estimated by the processing unit 230, and a cleavage stage determined and input by the embryologist.

Figure 7:
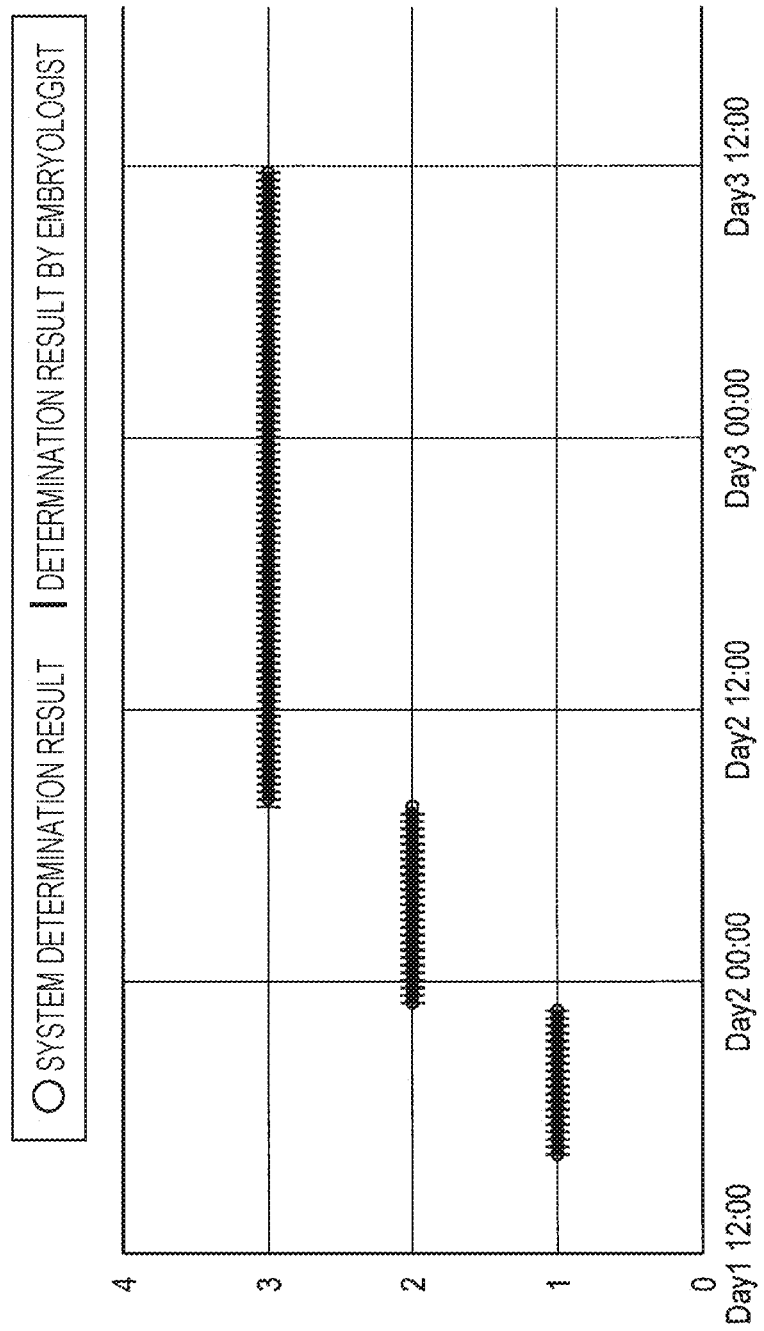
FIG. 7 is a diagram illustrating an example of comparative display of cleavage stages determined by a processing unit according to the same embodiment, and an embryologist.

FIG. 7 is a diagram illustrating an example of the comparative display of the cleavage stages determined by the processing unit 230 according to the present embodiment and an embryologist. In the example illustrated in FIG. 7, determination results of the cleavage stages related one-cell phase to four-cell phase by the processing unit 230 and the embryologist are illustrated in time series. Note that, in the example illustrated in FIG. 7, a determination result of a cleavage stage by the processing unit 230 is indicated by a round mark, and a determination result of a cleavage stage by the embryologist is indicated by a vertical stick mark.

Thus, the display control unit 240 according to the present embodiment can display, on the same graph, the determinations result of the cleavage stages by the processing unit 230 and the determination results of the cleavage stages by the embryologist. The above-described functions of the display control unit 240 according to the present embodiment enables the embryologist to intuitively grasp a difference from a determination result by the processing unit 230 and perform efficient work in a short time at the time when the embryologist determines the culture statuses related to the large amount of fertile ova.

Subsequently, estimation of a cleavage stage according to the present embodiment and the display control related to a result of the estimation will be described. As described above, since the processing unit 230 according to the present embodiment performs the morphological analysis on a captured image of a fertile ovum by using the learned model generated on the basis of the machine learning algorithm, a probability value related to the cleavage stage of the fertile ovum can be output in time series for each cleavage stage.

Since the processing unit 230 (also referred to as a recognizer or a classifier) performs the morphological analysis by using, for example, the learned knowledge learned on the basis of the training data and images of a fertile ovum having one cell, two cells, and three or more cells, it is possible to output a probability in which a fertile ovum of an input image has one cell, a probability in which the fertile ovum has two cell, and a probability value in which the fertile ovum has three or more cells. That is, the probability values related to the cell phases of the fertile ovum can be output by inputting, as input data, images of the fertile ovum to the learned model included in the processing unit 230.

At this time, the display control unit 240 according to the present embodiment may control time-series display of the above-described probability values output from the processing unit 230.

Figure 8:
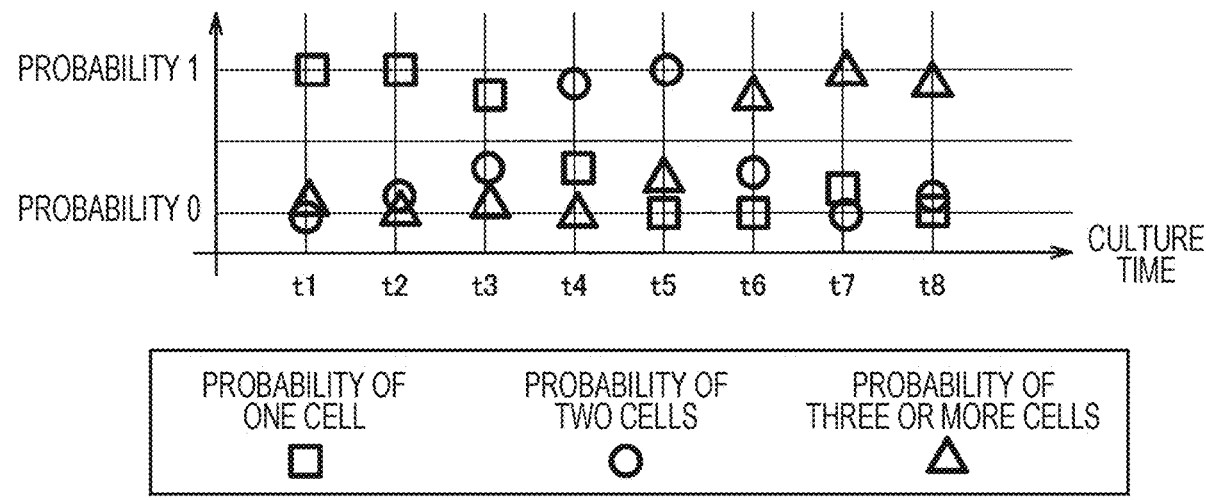
FIG. 8 is a diagram illustrating an exemplary graph generated on the basis of probability values of the cleavage stages according to the same embodiment.

FIG. 8 is a diagram illustrating an exemplary graph generated on the basis of probability values of the cleavage stages according to the present embodiment. In the exemplary case illustrated in FIG. 8, the display control unit 240 generates the graph obtained by plotting, along the time series, the probability values related to the cleavage stages output from the processing unit 230. Note that FIG. 8 illustrates the exemplary graph in a case where the processing unit 230 outputs the probability values related to one cell, two cells, and three or more cells on the basis of input images. Note that 1 is defined as 100% and 0 is defined as 0% for the above-described probability values.

The above-described functions of the processing unit 230 and the display control unit 240 according to the present embodiment enable an embryologist to easily grasp temporal changes in the probability values related to the cleavage stages of the fertile ovum.

Furthermore, the processing unit 230 according to the present embodiment may estimate a cleavage stage at each timepoint at which image capturing has been performed, for example, on the basis of the highest probability value of a cleavage stage out of probability values of respective cleavage stages calculated at each timepoint.

Figure 9:
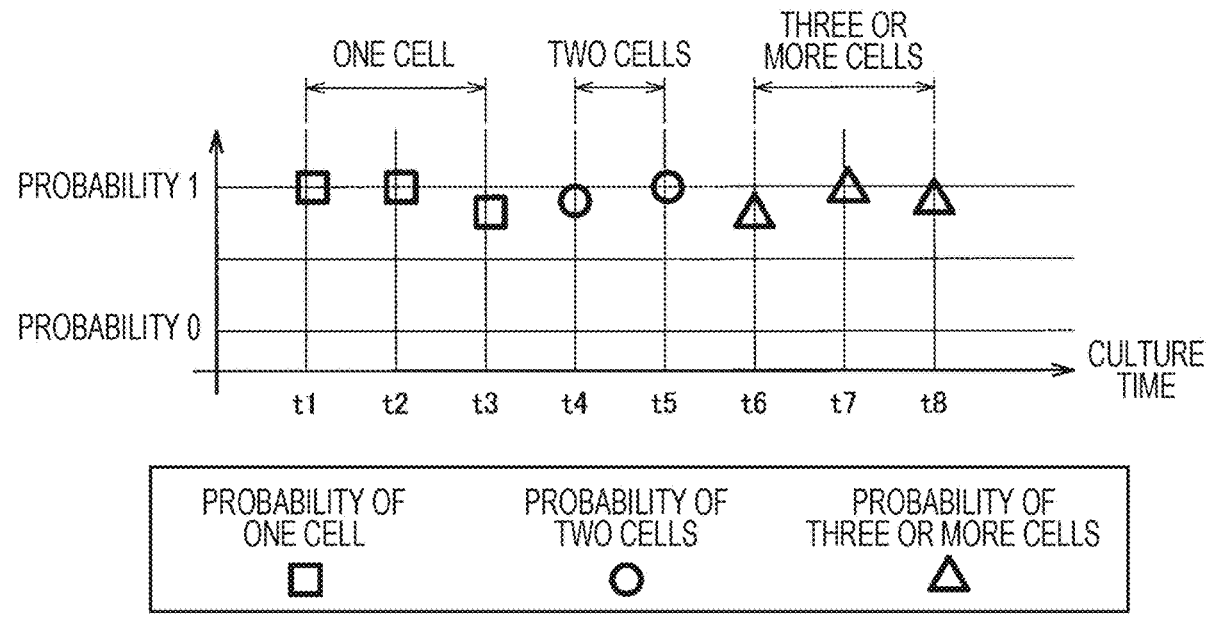
FIG. 9 is a diagram illustrating an exemplary graph generated on the basis of probability values of the cleavage stages according to the same embodiment.

At this time, the display control unit 240 according to the present embodiment generates a graph obtained by plotting only the highest probability value of the cleavage stage at each timepoint as illustrated, for example, in FIG. 9 and may add, onto the graph, information on the cleavage stages estimated by the processing unit 230.

The above-described functions of the processing unit 230 and the display control unit 240 according to the present embodiment enable an embryologist to intuitively grasp the temporal changes in each cleavage stage related to the fertile ovum.

Furthermore, the processing unit 230 according to the present embodiment may output a probability waveform obtained by interpolating the probability values of each cleavage stage between the timepoints at which images have been captured. At this time, the processing unit 230 according to the present embodiment can output a slope of the probability values and the above-described probability waveform which are learned on the basis of the images of the fertile ovum captured at a short time interval, for example, a 10-minute interval or the like.

The above-described function of the processing unit 230 according to the present embodiment makes it possible to acquire the probability value of each cleavage stage between the timepoints of image capturing even in a case where the interval of time-lapse image capturing at the time of actual use is set longer (for example, 30 minutes, 1 hour, or the like) than the interval at the time of learning, and it is possible to largely reduce a cost for the image capturing and the estimation.

Figure 10:
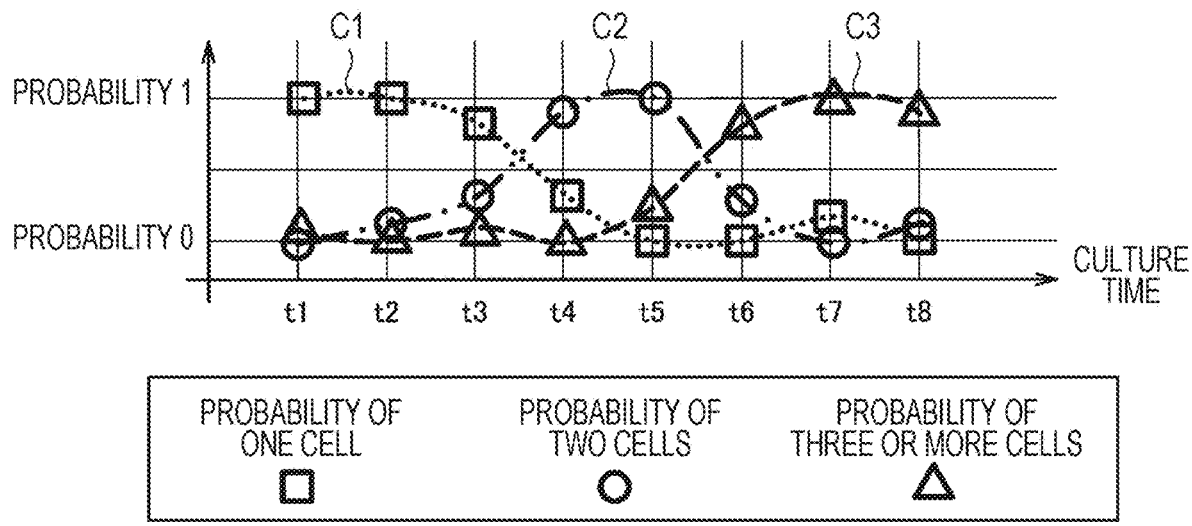
FIG. 10 is a diagram illustrating an exemplary graph generated on the basis of probability values of the cleavage stages according to the same embodiment.

Furthermore, at this time, the display control unit 240 according to the present embodiment may generate a graph including the probability waveforms output from the processing unit 230 as illustrated, for example, in FIG. 10. In an exemplary case illustrated in FIG. 10, the display control unit 240 generates the graph including a probability waveform C1 obtained by interpolating probability values of the one cell, a probability waveform C2 obtained by interpolating probability values of the two cells, and a probability waveform C3 obtained by interpolating probability values of the three or more cells.

Furthermore, the processing unit 230 according to the present embodiment can estimate cleavage timing on the basis of the acquired probability waveforms, and can further estimate a cleavage stage between respective timepoints on the basis of the cleavage timing.

For example, the processing unit 230 according to the present embodiment detects an intersection at which the probability waveforms related to the two cleavage stages intersect, and may estimate, as cleavage timing, a timepoint corresponding to the intersection.

Figure 11:
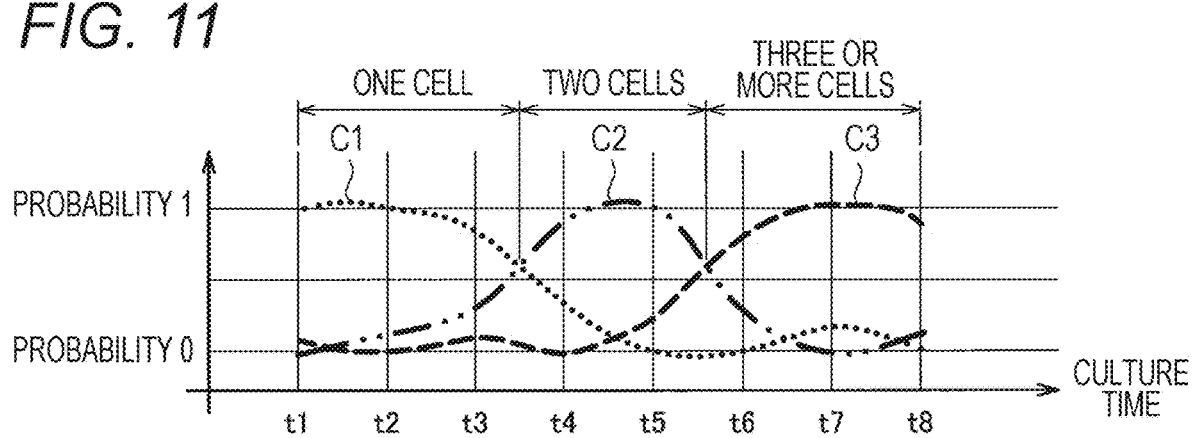
FIG. 11 is a diagram illustrating an exemplary graph generated on the basis of probability values of the cleavage stages according to the same embodiment.

For example, in a case of a graph illustrated in FIG. 11, the processing unit 230 may estimate, as cleavage timing from one cell to two cells, an intersection between the probability waveform C1 related to the one cell and the probability waveform C2 related to the two cells. Furthermore, the processing unit 230 can estimate, as cleavage timing from two cells to three or more cells, an intersection between the probability waveform C2 related to the two cells and the probability waveform C3 related to the three or more cells.

The above-described function of the processing unit 230 according to the present embodiment makes it possible to estimate a cleavage stage of a fertile ovum with a level of granularity finer than that of the image capturing interval, and an embryologist can grasp the culture status of the fertile ovum in more detail.

Figure 12:
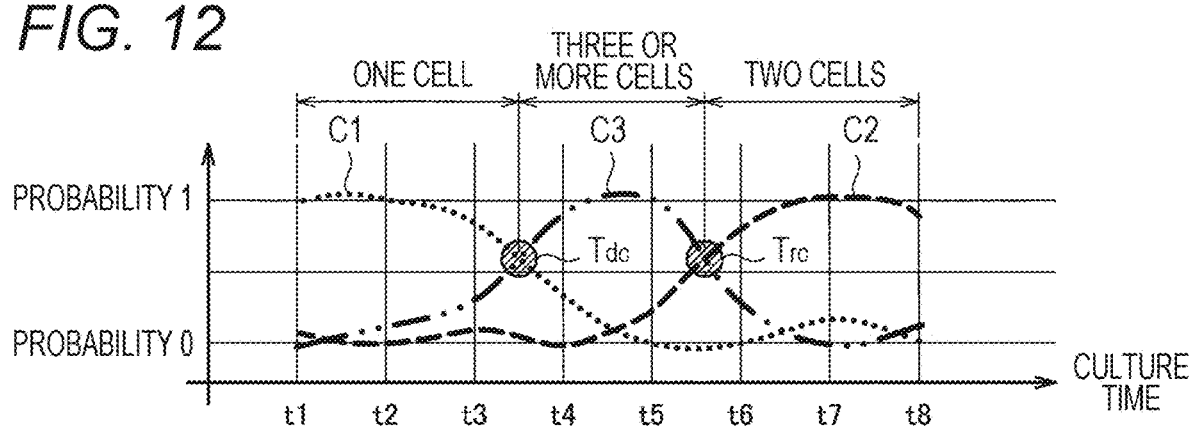
FIG. 12 is a diagram to describe abnormal cleavage estimation based on probability waveforms by the processing unit according to the same embodiment.
Figure 13:
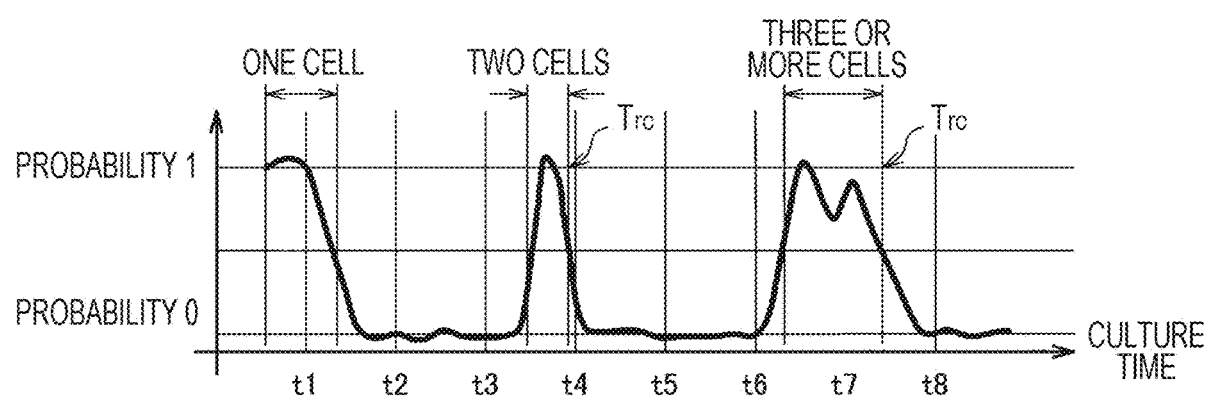
FIG. 13 is a diagram to describe abnormal cleavage estimation based on a probability waveform by the processing unit according to the same embodiment.

Furthermore, the processing unit 230 according to the present embodiment may estimate occurrence of abnormal cleavage of a fertile ovum and timing thereof on the basis of the acquired probability waveforms. FIGS. 12 and 13 are diagrams to describe abnormal cleavage estimation based on the probability waveforms by the processing unit 230 according to the present embodiment.

For example, in an exemplary case illustrated in FIG. 12, the processing unit 230 can estimate occurrence of direct cleavage from the one cell to the three or more cells by detecting an intersection where the probability waveform C1 related to the one cell intersects with the probability waveform C3 related to three or more cells. At this time, the processing unit 230 according to the present embodiment may output and detect, as direct cleavage occurrence timing $T_{do}$, the intersection between the probability waveform C1 and the probability waveform C3.

Furthermore, in the exemplary case illustrated in FIG. 12, the processing unit 230 can estimate occurrence of reverse cleavage from the three or more cells to two details by detecting an intersection where a probability waveform C3 related to the three or more cells intersects with a probability waveform C2 related to the two cells. At this time, the processing unit 230 according to the present embodiment may output and detect, as reverse cleavage occurrence timing $T_{rc}$, the intersection between the probability waveform C3 and the probability waveform C2.

Furthermore, the display control unit 240 according to the present embodiment may perform control such that the direct cleavage occurrence timing $T_{dc}$ and the reverse cleavage occurrence timing $T_{rc}$ detected as described above and the information related to the cleavage stages are displayed on the graph.

The above-described functions of the processing unit 230 and the display control unit 240 according to the present embodiment enable an embryologist to easily grasp the abnormal cleavage of a fertile ovum, and take a measure such as removing the fertile ovum, or the like.

Note that estimation of the abnormal cleavage according to the present embodiment is not limited to the above-described examples. The processing unit 230 according to the present embodiment can also estimate the abnormal cleavage of a fertile ovum on the basis of, for example, a probability waveform related to one certain cleavage stage.

For example, as illustrated in FIG. 13, the processing unit 230 outputs a probability waveform C1 related to one cell. At this time, the processing unit 230 can estimate, as a one-cell phase, a period in which the probability waveform C1 exceeds a threshold. Here, like the example illustrated in FIG. 13, for example, in a case of detecting a period estimated to be the one-cell phase again after the one-cell phase is finished and shifted to another cell phase, it is possible to estimate occurrence of the reverse cleavage.

Thus, the processing unit 230 according to the present embodiment can estimate occurrence of the abnormal cleavage related to a fertile ovum on the basis of various techniques. The processing unit 230 can also estimate occurrence of the direct cleavage in a case where, for example, the four-cell phase is estimated before the two-cell phase is estimated.

Next, estimation of the cleavage stages of the morula and thereafter according to the present embodiment will be described. Generally, it is said that the reverse cleavage in which a cleavage stage tracks back does not occur in the cleavage stage of the morula and thereafter. Therefore, the processing unit 230 according to the present embodiment can estimate a cleavage stage with higher accuracy on the assumption that no occurrence of the reverse cleavage.

FIGS. 14 to 17 are diagrams to describe estimation of cleavage stages of the morula and thereafter according to the present embodiment. Note that FIGS. 14 to 17 each illustrate an exemplary case where the processing unit 230 performs estimation related to the morula, the early blastocyst, the blastocyst, and the expanding blastocyst.

Figure 14:
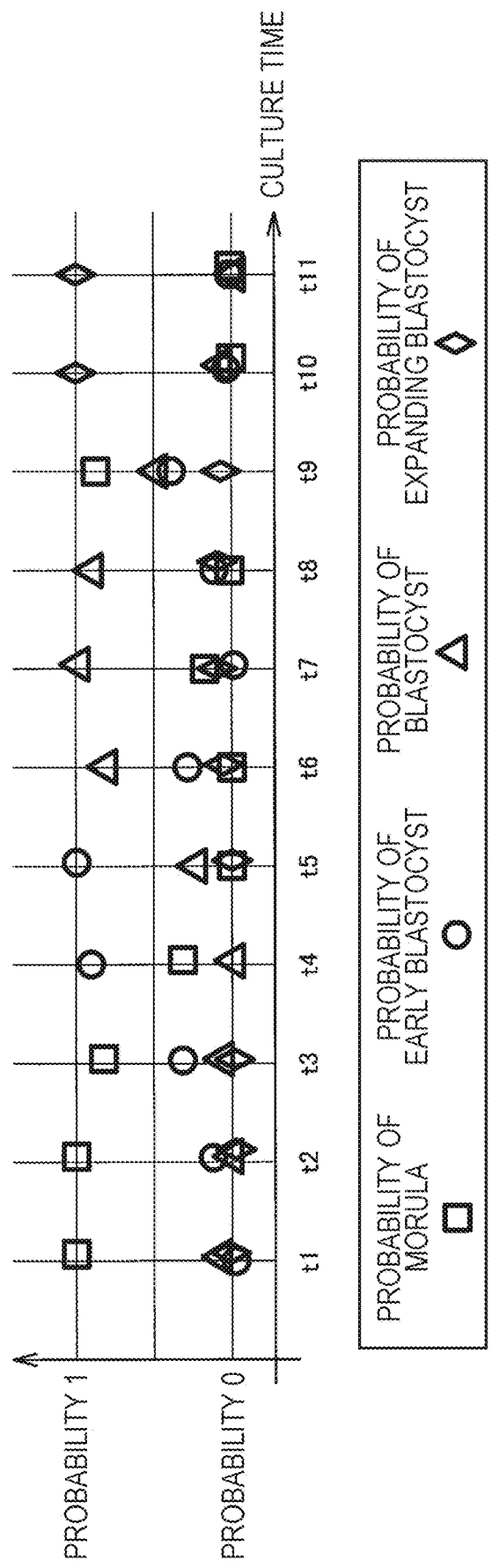
FIG. 14 is a diagram to describe estimation of cleavage stages of a morula and thereafter according to the same embodiment.
Figure 15:
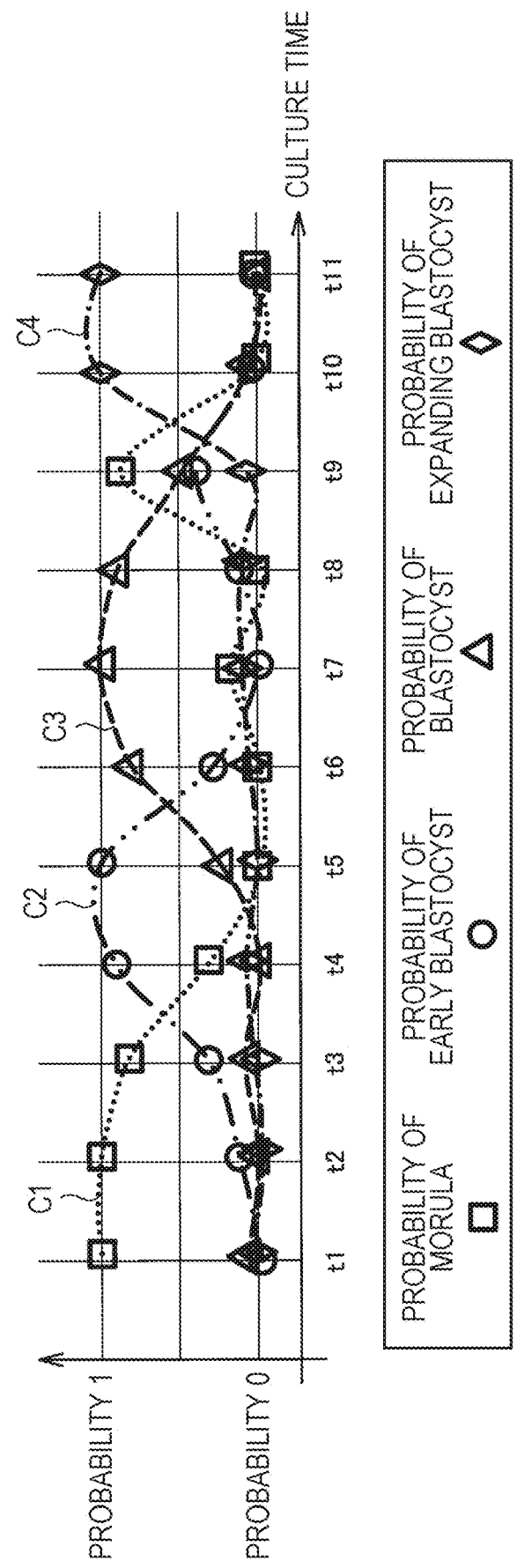
FIG. 15 is a diagram to describe the estimation of the cleavage stages of the morula and thereafter according to the same embodiment.

The processing unit 230 according to the present embodiment can output, by the above-described techniques, a probability value and a probability waveform for each of the cleavage stages of the morula and thereafter. FIG. 14 illustrates a graph generated by the display control unit 240 on the basis of the output probability values, and FIG. 15 illustrates a graph generated by the display control unit 240 on the basis of the output probability waveforms. Note that, in FIG. 15, the probability waveforms related to morula, the early blastocyst, the blastocyst, and the expanding blastocyst are indicated by reference signs C1 to C4, respectively.

Furthermore, as described above, the processing unit 230 can estimate a cleavage stage at each timepoint on the basis of the acquired probability waveforms and the like. At this time, in a case of not using the predicated knowledge that no reverse cleavage occurs in the cleavage stages of the morula and thereafter, the processing unit 230 erroneously estimates, as the morula, a cleavage stage at (near) a timepoint t9 on the basis of a probability value at the timepoint t9 as illustrated in FIG. 16.

Figure 16:
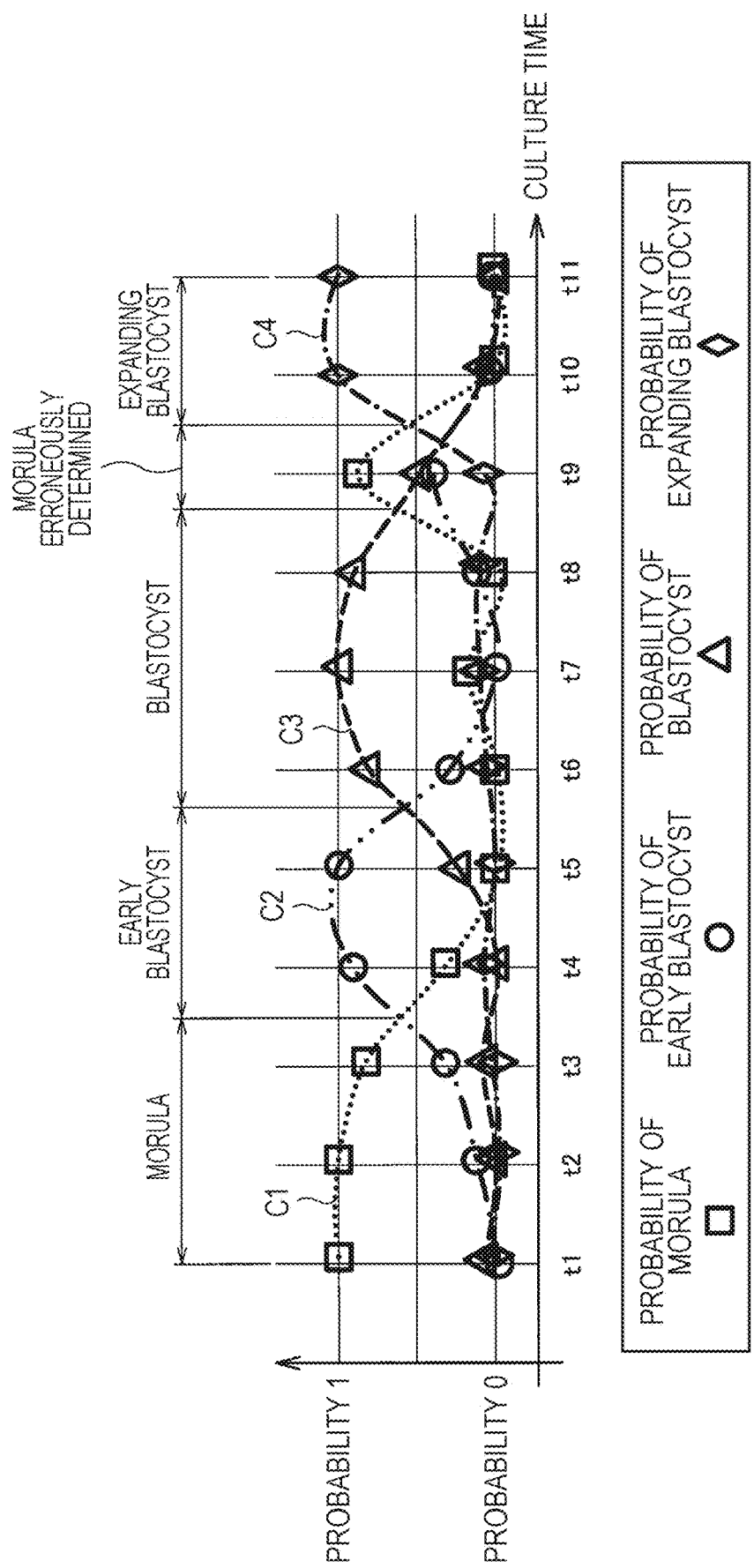
FIG. 16 is a diagram to describe the estimation of the cleavage stage of the morula and thereafter according to the same embodiment.
Figure 17:
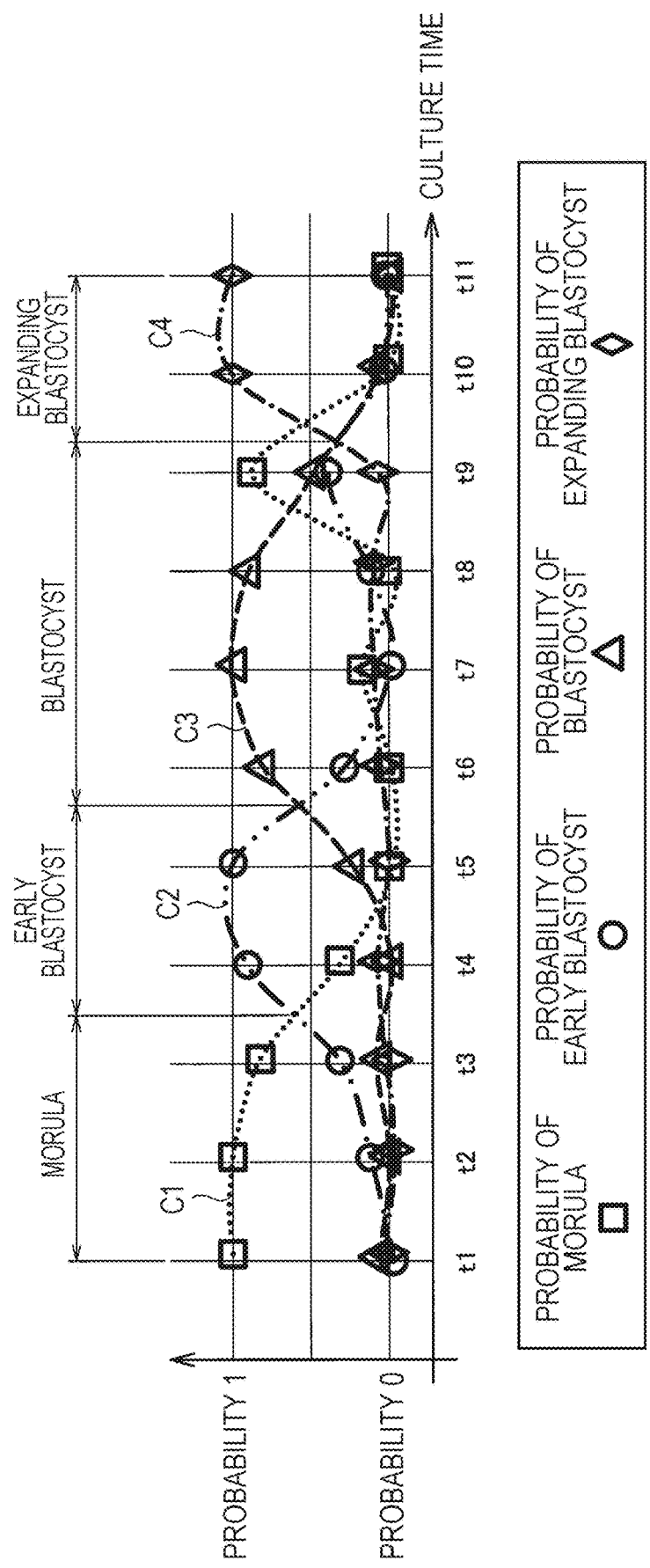
FIG. 17 is a diagram to describe the estimation of the cleavage stages of the morula and thereafter according to the same embodiment.

On the other hand, in a case where the processing unit 230 performs estimation by using the predicated knowledge that no reverse cleavage occurs in the cleavage stages of the morula and thereafter, the cleavage stage at (near) the timepoint t9 at which the cleavage stage has been erroneously determined as the morula in FIG. 16 can be corrected to the expanding blastocyst, as illustrated in FIG. 17.

Thus, the processing unit 230 according to the present embodiment makes it possible to effectively improve estimation accuracy of the cleavage stages of the morula and thereafter by using the predicated knowledge that no reverse cleavage occurs in the cleavage stages of the morula and thereafter.

Next, analysis related to a shape and the like of a culture target according to the present embodiment will be described. The processing unit 230 according to the present embodiment recognizes, for example, a shape of a culture target such as a fertile ovum, and analyzes a physical form such as the area and roundness of the culture target and characteristics thereof on the basis of a result of the recognition.

Furthermore, at this time, the display control unit 240 according to the present embodiment may generate a graph indicating temporal changes in the above-described recognition result and analysis result output from the processing unit 230, and may display the graph on the user interface UI.

Moreover, the display control unit 240 according to the present embodiment may generate an overlay image or the like on the basis of a recognition probability image output from the processing unit 230, and may display the overlay image together with the above-described graph.

FIG. 18 is a diagram to describe generation of an overlay image according to the present embodiment. An original image Io of a fertile ovum FA captured by the image capturing device 10 at a certain timepoint is schematically illustrated on the left side of FIG. 18. The processing unit 230 according to the present embodiment can output a recognition probability image related to the fertile ovum FA by executing shape recognition processing while using the above-described original image Io as an input.

Here, the above-described recognition probability image is obtained by visualizing probability distribution related to the recognition result of the culture target in the original image, and the image can indicate that for example, the closer to white a color is, the higher a probability that a subject (pixel) is the culture target is, and the closer to black a color is, the lower a probability that a subject (pixel) is the culture target is.

At this time, the display control unit 240 according to the present embodiment generates a binarized image obtained by binarizing, on the basis of a predetermined threshold, the recognition probability image from the processing unit 230, and the display control unit 240 can generate an overlay image Ir as illustrated on the right side of FIG. 18 by translucently overlaying the binarized image on the original captured image. Note that green or the like that can be easily recognized by an embryologist may be adopted as an overlay color, for example.

On the other hand, the display control unit 240 according to the present embodiment may display, together with the above-described graph, not only the overlay as described above but also various images indicating the recognition result related to the shape of the culture target. For example, the display control unit 240 may generate, on the basis of the above-described recognition probability image, a segmentation image indicating a segmentation result of a specific interest portion of the culture target in the image and may display the segmentation image together with the graph.

Figure 19:
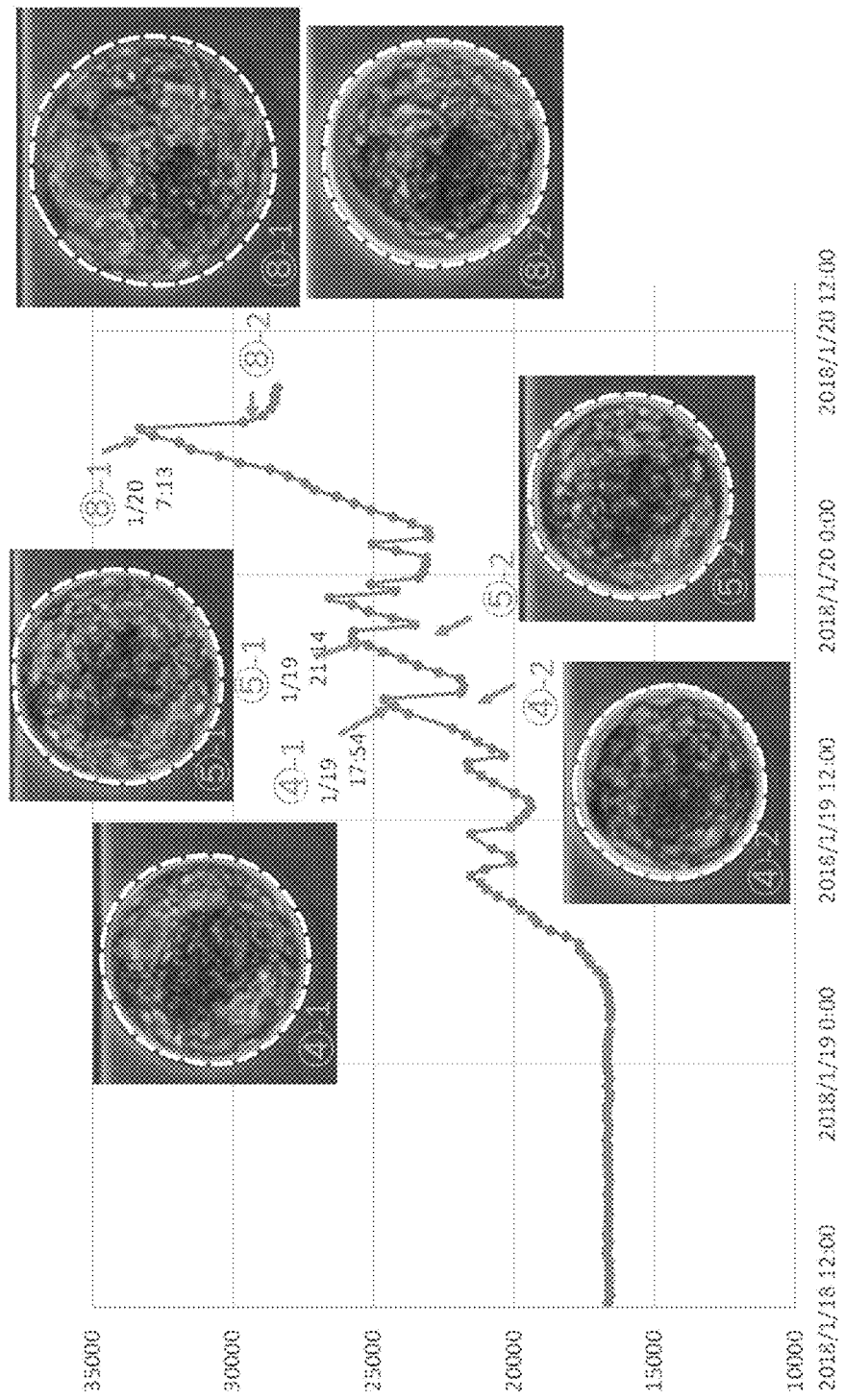
FIG. 19 is an exemplary graph generated on the basis of shape recognition results and analysis results of a culture target according to the present embodiment according to the same embodiment.

FIG. 19 is an exemplary graph generated on the basis of shape recognition results and analysis results of a culture target according to the present embodiment. Note that transition of the area of a fertile ovum is illustrated in a time series in the example illustrated in FIG. 19. Furthermore, FIG. 19 illustrates an exemplary case of adopting segmentation images as the images presented together with the graph. Furthermore, in FIG. 19, a plot on the graph and a segmentation image corresponding to the plot are indicated by the same number.

Thus, the processing unit 230 and the display control unit 240 according to the present embodiment can assist an embryologist to perform quality determination on a fertile ovum and the like, by performing processing on the image to obtain a state in which contraction or expansion of an entire region of the fertile ovum can be easily and visually checked as illustrated in FIG. 19, for example.

Furthermore, the shape recognition according to the present embodiment is not limited to an entire culture target, and may be a constituent included in the culture target or an arbitrary region of the constituent. FIG. 20 is a diagram to describe generation of an overlay image of a constituent included in a culture target according to the present embodiment. FIG. 20 schematically illustrates an exemplary overlay image Ir, in which the processing unit 230 according to the present embodiment outputs a recognition probability image related to a shape of a cell mass CM of a fertile ovum FA on the basis of an original image Io, and the display control unit 240 generates the overlay image Ir on the basis of the recognition probability image.

Figure 21:
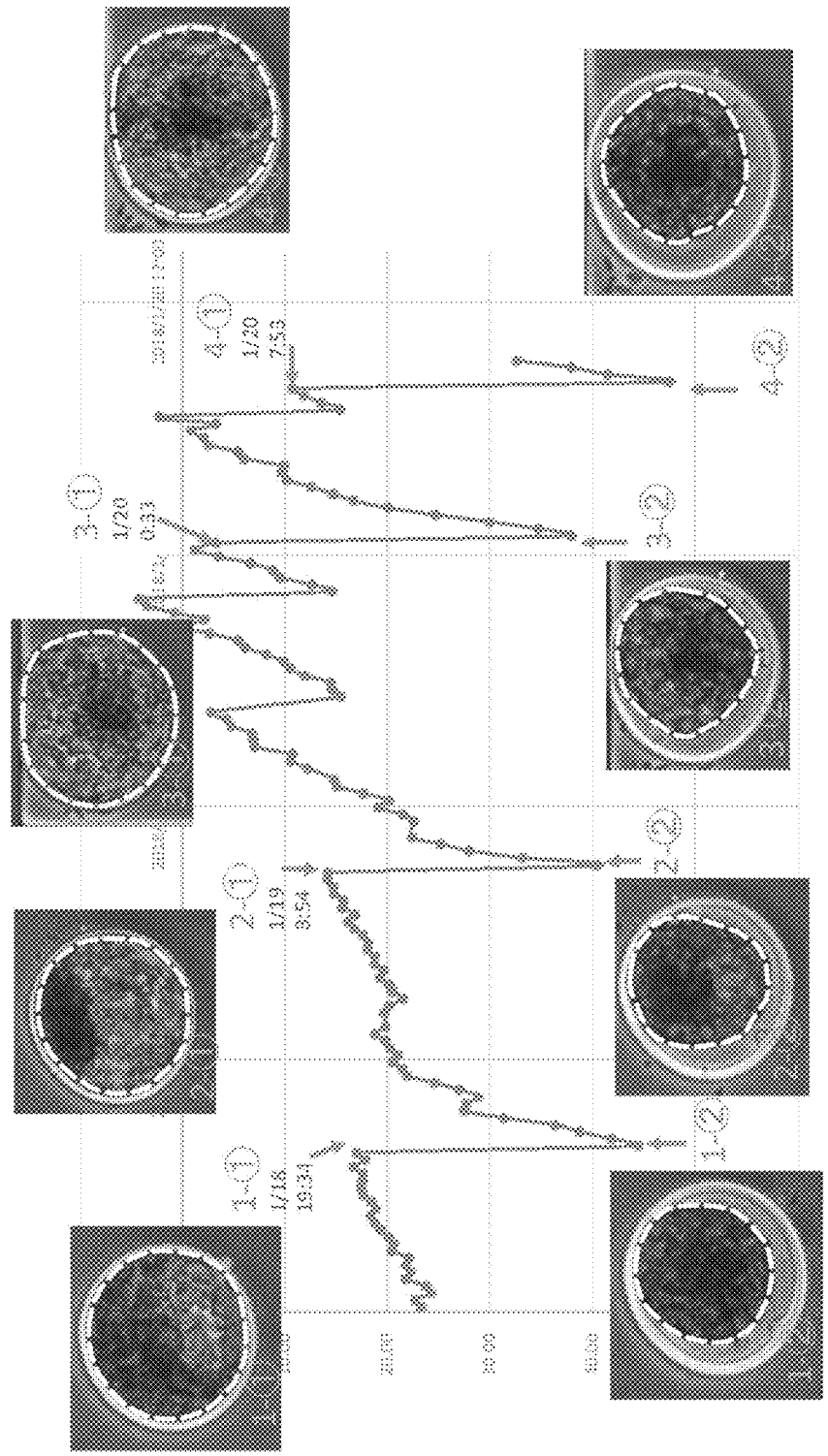
FIG. 21 is an exemplary graph generated on the basis of shape recognition results and analysis results of a constituent included in a nutrient target according to the same embodiment.
Figure 22:
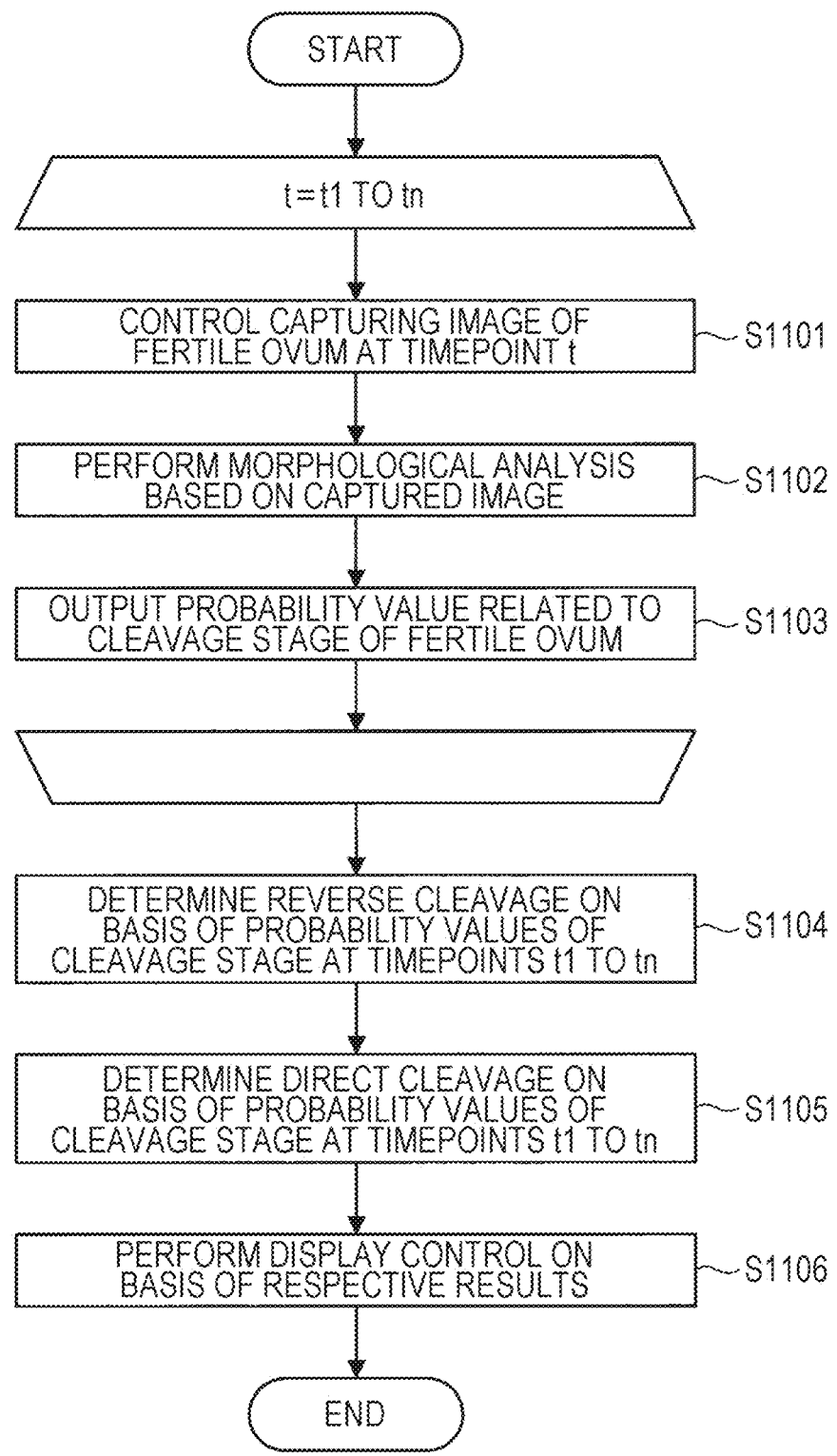
FIG. 22 is an exemplary flowchart illustrating an operation flow of a control device according to the same embodiment.

Furthermore, FIG. 21 is an exemplary graph generated on the basis of shape recognition results and analysis results of a constituent included in a culture target according to the present embodiment. Note that, in the example illustrated in FIG. 21, transition of the area of a cell mass included in the fertile ovum is illustrated in a time series. Furthermore, FIG. 21 illustrates the exemplary case where segmentation images are adopted as the images to be presented together with the graph. Furthermore, in FIG. 21, a plot on the graph and each segmentation image corresponding to the plot are indicated by the same number.

Thus, the processing unit 230 and the display control unit 240 according to the present embodiment make it possible to provide a user such as an embryologist with contraction and expansion of a region related to a constituent such as the cell mass included in the fertile ovum in a state easily and visually checked as illustrated, for example, in FIG. 21. Note that, the culture status according to the present embodiment includes not only the above-described examples but also a status of fertilization of a fertile ovum, a status of appearance/disappearance of pronuclei, a status of appearance/disappearance of a polar body, and the like. Furthermore, the culture status according to the present embodiment may include a status of fine fragmentation, a status of symmetry of a blastomere, a status of appearance of morula compaction, a status of appearance of an inner cell mass (ICM) and a trophectoderm (TE), a thickness or a status of hatching of a zona, and the like.

In the above, the recognition and the analysis by the processing unit 230 according to the present embodiment and the display control by the display control unit 240 according to the present embodiment have been described. Note that the display control unit 240 according to the present embodiment may display, on the user interface UI, the above-exemplified various graphs related to culture statuses of a plurality of culture targets such that comparison can be made between the plurality of culture targets. For example, the display control unit 240 may perform control so as to display, side by side, graphs corresponding to the plurality of culture targets in a manner similar to the time-lapse images illustrated in FIG. 1.

1.4. Operation Flow

Next, an operation flow of the control device 20 according to the present embodiment will be described in detail. FIG.

22 is an exemplary flowchart illustrating an operation flow of the control device 20 according to the present embodiment. Note that the description will be provided below for an exemplary case where a culture target according to the present embodiment is a fertile ovum and the processing unit 230 estimates a cleavage stage of the fertile ovum or occurrence of abnormal cleavage.

The control device 20 repeatedly executes following steps S1101 to S1104 at timepoints t=t1 to tn.

First, the image capturing control unit 210 controls the image capturing device 10 to capture an image of the fertile ovum at each timepoint t (S1101).

Next, the processing unit 230 performs morphological analysis based on the captured image of the fertile ovum in step S1101 (S1102).

Subsequently, the processing unit 230 outputs a probability value related to a cleavage stage of the fertile ovum as a result of the morphological analysis in step S1102 (S1103).

When the repeated processing related to steps S1101 to S1103 described above is finished, the processing unit 230 determines reverse cleavage on the basis of the probability values of the cleavage stage at the timepoints t1 to tn (S1104).

Furthermore, the processing unit 230 determines the direct cleavage on the basis of the probability values of the cleavage stage at the timepoints t1 to tn (S1105).

Next, the display control unit 240 performs display control of the user interface UI on the basis of respective results obtained in steps S1101 to S1105 (S1106).

2. Exemplary Hardware Configuration

Figure 23:
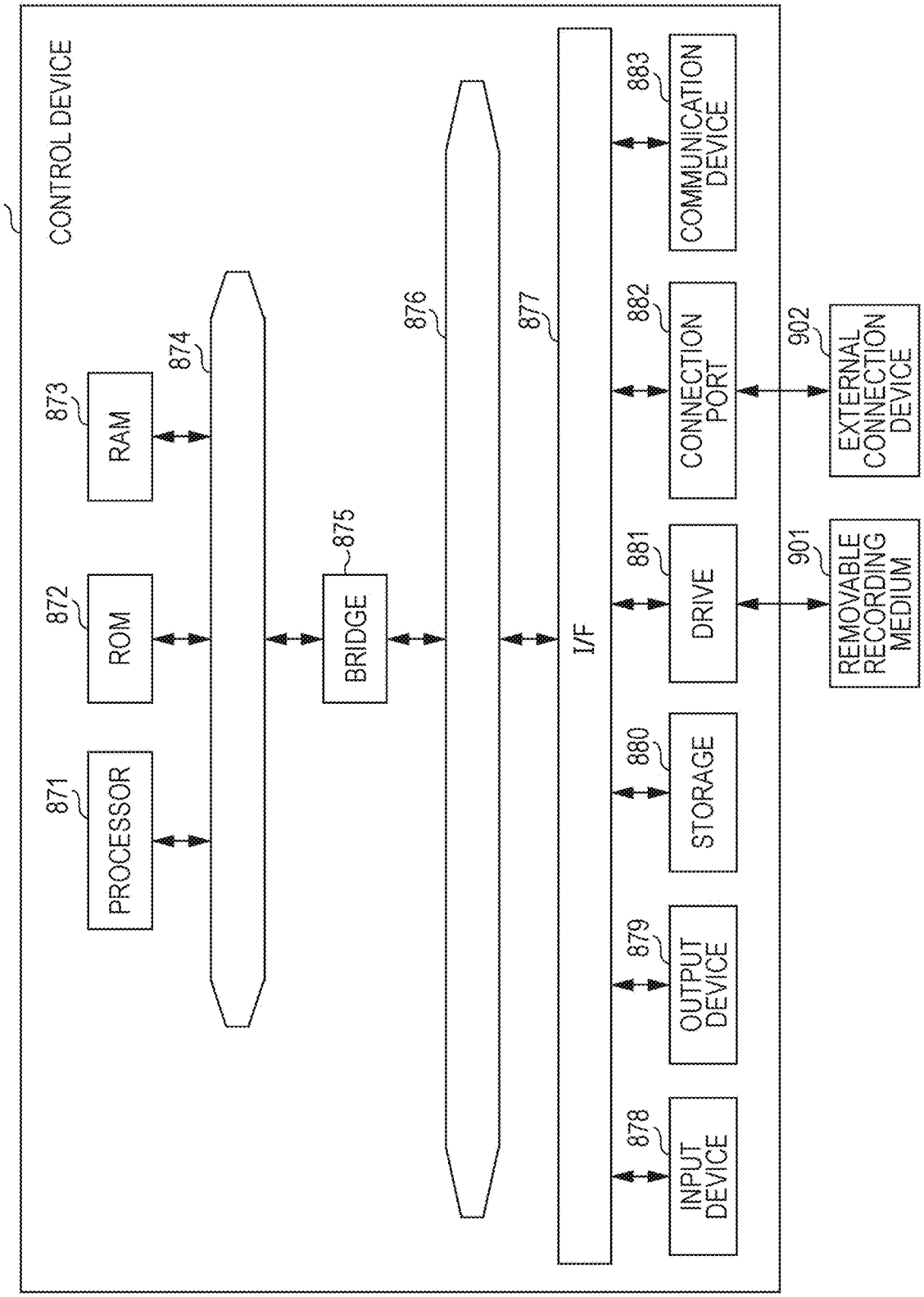
FIG. 23 is a diagram illustrating an exemplary hardware configuration of the control device according to an embodiment of the present disclosure.

Next, an exemplary hardware configuration of the control device 20 according to an embodiment of the present disclosure will be described. FIG. 23 is a block diagram illustrating an exemplary hardware configuration of the control device 20 according to the embodiment of the present disclosure. Referring to FIG. 23, the control device 20 includes, for example, a processor 871, a ROM 872, a RAM 873, a host bus 874, a bridge 875, an external bus 876, an interface 877, an input device 878, an output device 879, a storage 880, a drive 881, a connection port 882, and a communication device 883. Note that the hardware configuration illustrated here is an example, and some of constituent elements may be omitted. Furthermore, a constituent element other than the constituent elements illustrated herein may be further included.

(Processor 871) The processor 871 functions as, for example, an arithmetic processing device or a control device, and controls entire or partial operation of each of the constituent elements on the basis of various programs recorded in the ROM 872, the RAM 873, the storage 880, or a removable recording medium 901.

(ROM 872 and RAM 873) The ROM 872 is a means that stores a program read by the processor 871, data used for arithmetic operation, and the like. The RAM 873 temporarily or permanently stores, for example, a program read by the processor 871, various parameters, and the like which are changed as appropriate at the time of executing the program.

(Host Bus 874, Bridge 875, External Bus 876, and Interface 877)

The processor 871, the ROM 872, and the RAM 873 are mutually connected via, for example, the host bus 874 capable of performing high-speed data transmission. Here, the host bus 874 is connected to, via the bridge 875, the external bus 876 that performs a relatively low-speed data transmission, for example. Furthermore, the external bus 876 is connected to the various constituent elements via the interface 877.

(Input Device 878) For the input device 878, a mouse, a keyboard, a touch panel, a button, a switch, a lever, and the like are used, for example. Furthermore, as the input device 878, a remote controller (hereinafter referred to as a remote controller) capable of transmitting a control signal by utilizing infrared rays or other radio waves may also be used. Furthermore, the input device 878 includes a voice input device such as a microphone.

(Output Device 879) The output device 879 is a device capable of visually or audibly notify a user of acquired information, and includes, for example, a display device of a cathode ray tube (CRT), an LCD, an organic EL, or the like, an audio output device such as a speaker and a headphone, a printer, a mobile phone, a facsimile, or the like. Furthermore, the output device 879 according to the present disclosure includes various vibration devices capable of outputting tactile stimuli.

(Storage 880) The storage 880 is a device to store various kinds of data. As the storage 880, for example, a magnetic storage device such as a hard disk drive (HDD), a semiconductor storage device, an optical storage device, a magneto-optical storage device, or the like is used.

(Drive 881) The drive 881 is a device that reads information recorded in the removable recording medium 901 such as a magnetic disk, an optical disc, a magneto-optical disc, or a semiconductor memory, or writes information in the removable recording medium 901, for example.

(Removable Recording Medium 901) The removable recording medium 901 includes, for example, a DVD medium, a Blu-ray (registered trademark) medium, an HD/DVD media, various kinds of semiconductor storage media, or the like. Needless to mention, the removable recording medium 901 may include, for example: an IC card on which a non-contact IC chip is mounted; an electronic device; or the like.

(Connection Port 882)

The connection port 882 is a port to connect, for example, an externally-connected device 902 like a universal serial bus (USB) port, an IEEE 1394 port, a small computer system interface (SCSI), an RS-232C port, or an optical audio terminal, or the like.

(Externally-Connected Device 902) The externally-connected device 902 includes, for example, a printer, a portable music player, a digital camera, a digital video camera, an IC recorder, or the like.

(Communication Device 883) The communication device 883 includes a communication device to provide connection to a network and includes, for example: a communication card for wired or wireless LAN, Bluetooth (registered trademark), or a wireless USB (WUSB); a router for optical communication; a router for an asymmetric digital subscriber line (ADSL); various kinds of communication modems; or the like.

3. Conclusion

As described above, the control device 20 according to the embodiment of the present disclosure includes the display control unit 240 that controls dynamic display related to a culture status of a culture target including a cell having a division potential, and the culture status is estimated along the time series by the morphological analysis using the learned model generated on the basis of the machine learning algorithm. Furthermore, the display control unit 240 according to the embodiment of the present disclosure has the characteristic of controlling the comparative display of the culture statuses related to the plurality of culture targets. With this configuration, the culture statuses related to the plurality of culture targets can be effectively visualized.

While the preferred embodiments of the present disclosure have been described in detail with reference to the attached drawings, the technical scope of the present disclosure is not limited to the examples. It is obvious that a person having ordinary skill in the technical field of the present disclosure can readily conceive various modified examples or revised examples within the scope of the technical idea described in the claims, and it should be understood that these examples are also included in the technical scope of the present disclosure.

Furthermore, the effects described in the present specification are merely illustrative or exemplary and are not limited. That is, the technology according to the present disclosure can provide, in addition to or instead of the above-described effects, another effect that may be obvious to those skilled in the art from the description of the present specification.

Furthermore, it is also possible to create a program causing hardware such as a CPU, a ROM, and a RAM built in a computer to exert functions equivalent to those of the configuration included in the control device 20, and it is also possible to provide a computer-readable recording medium in which the program is recorded.

Furthermore, the respective steps related to the processing of the control device 20 of the present specification may not necessarily be processed in the time series along the sequence described in the flowchart. For example, the respective steps related to the processing of the control device 20 may be processed in a sequence different from the sequence described in the flowchart, or may be processed in parallel.

Note that the following configurations are also included in the technical scope of the present disclosure.

(1)

A control device including a display control unit that controls dynamic display related to a culture status of a culture target including a cell having a division potential, the culture status being estimated along a time series by morphological analysis using a learned model generated on the basis of a machine learning algorithm, in which the display control unit controls comparative display of the culture statuses of a plurality of the culture targets.

(2)

The control device recited in (1) above, in which the cell having the division potential includes a fertile ovum.

(3)

The control device recited in (2) above, in which the culture status includes a cleavage status, and the display control unit controls comparative display related to the cleavage statuses of the plurality of fertile ova.

(4)

The control device recited in (3) above, in which the cleavage status includes a cleavage stage, and the display control unit performs comparative display related to the cleavage stages of the plurality of fertile ova.

(5)

The control device recited in (3) or (4) above, in which the cleavage status includes an occurrence status of abnormal cleavage, and the display control unit controls comparative display related to occurrence statuses of the abnormal cleavage of the plurality of fertile ova.

(6)

The control device recited in (5) above, in which the abnormal cleavage includes at least any one of direct cleavage or reverse cleavage.

(7)

The control device recited in any one of (2) to (6) above, in which the culture status includes a status related to a dead cell of the fertile ovum, and the display control unit controls comparative display of statuses related to the dead cells of the plurality of fertile ova.

(8)

The control device recited in any one of (2) to (7) above, in which the culture status includes a status related to at least any one of fertilization, a pronucleus, a polar body, fragmentation, a blastomere, compaction of a morula, an inner cell mass, a trophectoderm, or a zona of the fertile ovum.

(9)

The control device recited in any one of (2) to (8) above, in which the display control unit controls time-series display related to the culture status of the fertile ovum.

(10)

The control device recited in (9) above, in which the display control unit controls time-series display of probability values related to the cleavage stage of the fertile ovum estimated on the basis of captured images.

(11)

The control device recited in (10), in which the display control unit controls display of a probability waveform obtained by interpolating the probability values of the cleavage stage between timepoints at which the images are captured.

(12)

The control device recited in (10) or (11) above, in which the display control unit controls display related to cleavage timing of the fertile ovum estimated on the basis of the probability values.

(13)

The control device recited in any one of (10) to (12) above, in which the display control unit controls display of occurrence timing related to abnormal cleavage of the fertile ovum estimated on the basis of the probability values.

(14)

The control device recited in (9) above, in which the display control unit controls display related to an estimated lag-phase of the fertile ovum.

(15)

The control device recited in any one of (2) to (14) above, in which the display control unit displays the culture statuses of the plurality of fertile ova in a manner correlated to physical positions of the fertile ova in a culture dish.

(16)

The control device recited in any one of (1) to (15) above, further including a processing unit that uses a captured image of the culture target as an input, and dynamically estimates the culture status of the culture target in the time series by the morphological analysis using the learned model generated on the basis of the machine learning algorithm.

(17)

The control device recited in (16) above, in which the cell having the division potential includes a fertile ovum, and the processing unit outputs, in the time series, probability values related to cleavage stage of the fertile ovum by the morphological analysis.

(18)

The control device recited in (17) above, in which the processing unit estimates occurrence of abnormal cleavage of the fertile ovum on the basis of a probability waveform obtained by interpolating the probability values of the cleavage stage between timepoints at which the images are captured.

(19)

The control device recited in (18) above, in which the processing unit outputs the probability waveform on the basis of a slope of the probability values learned on the basis of the images captured at short intervals.

(20)

The control device recited in (1) to (19) above, in which the learned model is a recognizer generated by using learning data including: an image obtained by capturing an image of the culture target; and information associated with a characteristic related to at least one of a shape, a morphology, or a structure of the culture target.

(21)

A control method including controlling, by a processor, dynamic display related to a culture status of a culture target including a cell having a division potential, the culture status being estimated along a time series by morphological analysis using a learned model generated on the basis of a machine learning algorithm, and controlling the display further including controlling comparative display of the culture statuses of a plurality of the culture targets.

(22)

A program causing a computer to function as a control device including a display control unit that controls dynamic display related to a culture status of a culture target including a cell having a division potential, the culture status being estimated along a time series by morphological analysis using a learned model generated on the basis of a machine learning algorithm, in which the display control unit controls comparative display of the culture statuses of a plurality of the culture targets.

REFERENCE SIGNS LIST

10 Image capturing device
110 Image capturing unit
120 Holding unit
130 Light emission unit
20 Control device
210 Image capturing control unit
220 Learning unit
230 Processing unit
240 Display control unit
250 Communication unit
30 Display apparatus
310 Display unit

The invention claimed is:

1. A control device comprising:
a display controller including processing circuitry configured to control dynamic display related to a culture status of a culture target including a cell having a division potential, the culture status being estimated along a time series by morphological analysis using a learned model generated on a basis of a machine learning algorithm,
wherein the display controller is configured to control comparative display of the culture statuses of a plurality of the culture targets, wherein the cell having the division potential includes a fertile ovum and wherein the culture status includes a cleavage status, and the display controller is configured to control comparative display related to the cleavage statuses of the plurality of fertile ova.

2. The control device according to claim 1, wherein the cleavage status includes a cleavage stage, and the display controller is configured to control comparative display related to the cleavage stages of the plurality of fertile ova.

3. The control device according to claim 1, wherein the cleavage status includes an occurrence status of abnormal cleavage, and
the display controller is configured to control comparative display related to occurrence statuses of the abnormal cleavage of the plurality of fertile ova.

4. The control device according to claim 3, wherein the abnormal cleavage includes at least one of direct cleavage or reverse cleavage.

5. A control device comprising:
a display controller including processing circuitry configured to control dynamic display related to a culture status of a culture target including a cell having a division potential, the culture status being estimated along a time series by morphological analysis using a learned model generated on a basis of a machine learning algorithm,
wherein the display controller is configured to control comparative display of the culture statuses of a plurality of the culture targets, wherein the cell having the division potential includes a fertile ovum, and
wherein the culture status includes a status related to a dead cell of the fertile ovum, and
the controller is configured to control comparative display of statuses related to the dead cells of the plurality of fertile ova.

6. The control device according to claim 1, wherein the culture status includes a status related to at least any one of fertilization, a pronucleus, a polar body, fragmentation, a blastomere, compaction of a morula, an inner cell mass, a trophectoderm, or a zona of the fertile ovum.

7. The control device according to claim 1, wherein the display controller is configured to control time-series display related to the culture status of the fertile ovum.

8. A control device comprising:
a display controller including processing circuitry configured to control dynamic display related to a culture status of a culture target including a cell having a division potential, the culture status being estimated along a time series by morphological analysis using a learned model generated on a basis of a machine learning algorithm,
wherein the display controller is configured to control comparative display of the culture statuses of a plurality of the culture targets, wherein the cell having the division potential includes a fertile ovum,
wherein the display controller is configured to control time-series display related to the culture status of the fertile ovum, and wherein the display controller is configured to control time-series display of probability values related to a cleavage stage of the fertile ovum estimated on a basis of captured images.

9. The control device according to claim 8, wherein the display controller is configured to control display of a probability waveform obtained by interpolating the probability values of the cleavage stage between time-points at which the images are captured.

10. The control device according to claim 8, wherein the display controller is configured to control display related to cleavage timing of the fertile ovum estimated on a basis of the probability values.

11. The control device according to claim 8, wherein the display controller is configured to control display of occurrence timing related to abnormal cleavage of the fertile ovum estimated on a basis of the probability values.

12. A control device comprising:
a display controller including processing circuitry configured to control dynamic display related to a culture status of a culture target including a cell having a division potential, the culture status being estimated along a time series by morphological analysis using a learned model generated on a basis of a machine learning algorithm,
wherein the display controller is configured to control comparative display of the culture statuses of a plurality of the culture targets, wherein the cell having the division potential includes a fertile ovum,
wherein the display controller is configured to control time-series display related to the culture status of the fertile ovum, and
wherein the display controller is configured to control display related to an estimated lag-phase of the fertile ovum.

13. The control device according to claim 1, wherein the display controller is configured to control the culture statuses of the plurality of fertile ova in a manner correlated to well positions where the fertile ova are arranged in a culture dish.

14. A control device comprising:
a display controller including processing circuitry configured to control dynamic display related to a culture status of a culture target including a cell having a division potential, the culture status being estimated along a time series by morphological analysis using a learned model generated on a basis of a machine learning algorithm,
wherein the display controller is configured to control comparative display of the culture statuses of a plurality of the culture targets, further comprising
a processing unit configured to use a captured image of the culture target as an input, and dynamically estimate the culture status of the culture target in the time series by the morphological analysis using the learned model generated on a basis of the machine learning algorithm.

15. The control device according to claim 14, wherein the cell having the division potential includes a fertile ovum, and the processing unit is configured to output, in the time series, probability values related to cleavage stage of the fertile ovum by the morphological analysis.

16. The control device according to claim 15, wherein the processing unit is configured to estimate occurrence of abnormal cleavage of the fertile ovum on a basis of a probability waveform obtained by interpolating the probability values of the cleavage stage between time-points at which the images are captured.

17. The control device according to claim 16, wherein the processing unit is configured to output the probability waveform on a basis of a slope of the probability values learned on a basis of the images captured at short intervals.

18. A control device comprising:
a display controller including processing circuitry configured to control dynamic display related to a culture status of a culture target including a cell having a division potential, the culture status being estimated along a time series by morphological analysis using a learned model generated on a basis of a machine learning algorithm,
wherein the display controller is configured to control comparative display of the culture statuses of a plurality of the culture targets, and
wherein the learned model is a recognizer generated by using learning data including: an image obtained by capturing an image of the culture target; and information associated with a characteristic related to at least one of a shape, a morphology, or a structure of the culture target.

19. A control method comprising
controlling, by a processor, dynamic display related to a culture status of a culture target including a cell having a division potential, the culture status being estimated along a time series by morphological analysis using a learned model generated on a basis of a machine learning algorithm, wherein controlling further includes controlling comparative display of the culture statuses of a plurality of the culture targets, wherein the cell having the division potential includes a fertile ovum, wherein the culture status includes a cleavage status, and wherein controlling includes controlling comparative display related to the cleavage statuses of the plurality of fertile ova.

20. A non-transitory computer readable medium storing instructions that, when executed by processing circuitry, perform a control method comprising:
controlling dynamic display related to a culture status of a culture target including a cell having a division potential, the culture status being estimated along a time series by morphological analysis using a learned model generated on a basis of a machine learning algorithm,
wherein controlling further includes controlling comparative display of the culture statuses of a plurality of the culture targets, wherein the cell having the division potential includes a fertile ovum, wherein the culture status includes a cleavage status, and wherein controlling includes controlling comparative display related to the cleavage statuses of the plurality of fertile ova.

* * * * *